US009777047B2

(12) United States Patent
Vance et al.

(10) Patent No.: US 9,777,047 B2
(45) Date of Patent: Oct. 3, 2017

(54) ENDOGENOUS REGULATOR OF RNA SILENCING IN PLANTS

(71) Applicant: University of South Carolina, Columbia, SC (US)

(72) Inventors: Vicki Sue Vance, Columbia, SC (US); Lewis H. Bowman, Columbia, SC (US); Matthew W. Endres, Columbia, SC (US)

(73) Assignee: University of South Carolina, Columbia, SC (US)

( * ) Notice: Subject to any disclaimer, the term of this patent is extended or adjusted under 35 U.S.C. 154(b) by 597 days.

(21) Appl. No.: 14/252,408

(22) Filed: Apr. 14, 2014

(65) Prior Publication Data

US 2014/0366225 A1 Dec. 11, 2014

Related U.S. Application Data

(62) Division of application No. 11/921,385, filed as application No. PCT/US2005/019400 on Jun. 2, 2005, now Pat. No. 8,735,653.

(51) Int. Cl.
*C12N 15/82* (2006.01)
*C07K 14/415* (2006.01)
*C07K 16/14* (2006.01)

(52) U.S. Cl.
CPC ............ *C07K 14/415* (2013.01); *C07K 16/14* (2013.01); *C12N 15/8218* (2013.01)

(58) Field of Classification Search
None
See application file for complete search history.

(56) References Cited

U.S. PATENT DOCUMENTS 5,262,316 A * 11/1993 Engler ............... C12N 15/8205
800/294
6,664,446 B2 12/2003 Heard et al.
2004/0078852 A1 4/2004 Thomashow et al.

FOREIGN PATENT DOCUMENTS

WO WO 02/16655 2/2002

OTHER PUBLICATIONS

Li et al (PLoS One, 2015, 10(2): e0118056).*
GenBank AF478458.1 (published Dec. 2004).*
Kim et al (BBA—Gene Structure and Expression, 2005, 1729(3): 141-146; available online May 31, 2005).*
Abstract—Kim, et al., "Identification of a CaRAV1 Possessing an AP2/ERF and B3 DNA-binding domain from pepper leaves infected with Xanthomonas Axonopoddis pv. Glycines 8ra by Differential Display", Biochim, Biophys. Acta 1729: 141-146 (2005).
Baulcombe (Nature, 431, pp. 356-363, 2004).
Chapman (Genes and Dev, 18, pp. 1179-1186, 2004).
Horesh et al. (Bioinformatics, 19(2), pp. ii73-ii80, 2003).
Endres et al. (ASPB Abstract # 836, Jul. 24, 2004-Jul. 28, 2004; see attached PDF).
Wright, D.A. Townsend, J.A., Winfrey, R.J., Irwin, P.A., Rajagopal, J., Lonosky, P.M., Hall, B.D., Jondle, M.D. and Voytas, D.F. (2005), High-frequency homologous recombination in plants mediated by zinc-finger nucleases. The Plant Journal, 44: 693-705. doi: 10.1111/j.1365-313X.2005.02551.x.
Koprivova, A., Stemmer, C., Altmann, F., Hoffmann, A., Kopriva, S., Gorr, G., Reski, R. and Decker, E.L. (2004), Targeted knockouts of Physcomitrella lacking plant-specific immunogenic N-glycans. Plant Biotechnology Journal, 2: 517-523. Doi: 10.1111/j.1467-7652.2004.00100.x.
Yu Xin Hu, Yong Hong Wang, Xin Fang Liu, Jia Yang Li, Arabidopsis RAV1 is down-regulated by brassinosteriod and may act as a negative regulator during plant development, Cell Research, Feb. 2004, 14(1):8-15.
Kim et al., Biochim. Biophys. Acta 1729:141-146 (2005).
Baulcombe, Nature, 431:356-363 (2004).
Chapman, Genes and Dev., 18:1179-1186 (2004).
Horesh et al., Bioinformatics, 19(2):ii73-ii80 (2003).
Endres et al., ASPB Abstract #836, (Jul. 2004).
Wright et al., Plant Journal, 44:693-705 (2005).
Koprivova et al., Plant Biotech. Journal, 2:517-523 (2004).
Hu et al., Cell Research, 14(1):8-15 (2004).
GenBank Acc. No. AF478458, Dec. 15, 2004.

* cited by examiner

*Primary Examiner* — Elizabeth McElwain
*Assistant Examiner* — Stephen Uyeno
(74) *Attorney, Agent, or Firm* — Dority & Manning, PA

(57) ABSTRACT

Compositions and methods are described which use RAV proteins and genes that encode such proteins to regulate RNA silencing in plant cells. Novel ntRAV proteins and genes are also described.

4 Claims, 13 Drawing Sheets

FIG. 5

| Arabidopsis Genes | AA* | AP2 | B3 |
|---|---|---|---|
| ntRAV vs At1g13260 | 69.3 | 91.5 | 90.0 |
| vs At1g68840 | 71.8 | 91.5 | 88.1 |
| vs At1g51120 | 48.6 | 64.8 | 68.4 |
| vs At1g50680 | 54.2 | 60.7 | 68.4 |
| vs At1g25560 | 74.0 | 89.8 | 83.0 |
| vs At3g25730 | 77.9 | 94.9 | 44.4 |
| At1g13260 vs At1g68840 | 73.9 | | |
| Pepper Gene | | | |
| ntRAV vs gi|33320073|gb|AAQ05799.1 | 86.8 | 96.8 | 96.9 |
| Rice Genes | | | |
| ntRAV vs gi|34911404|ref|NP_917049.1 | 68.5 | 93.1 | 89.7 |
| vs gi|50932645|ref|XP_475850.1 | 68.5 | 93.1 | 89.6 |
| vs gi|34895690|ref|NP_909194.1 | 71.6 | 93.2 | 96.9 |
| vs gi|34895676|ref|NP_909187.1 | 68.2 | 87.7 | 86.5 |

Notes: AA, AP2 and B3 show percent amino acid similarity between ntRAV and the listed RAV protein.

FIG. 6A ntRAV vs. Arabidopsis RAVs

~ - no corresponding sequence and beginning or end

. - Sequence Gaps

A - Identical Sequence a - Non-Identical Sequence

```
at1g50680 ~~~~~~~~~~ ~~~~~~~~~~ ~~~~~~~~~~ ~~~~~~~~~~ ~~~~~~~~~~
at1g51120 ~~~~~~~~~~ ~~~~~~~~~~ ~~~~~~~~~~ ~mdemsnvak tttetsGltd
at1g25560 MeySCvDd.S SttseSlSis ttpkptttTe kKLSSpPAts mRLYRMGSGG
at1g68840 MdsSCiDeiS SatseSfS.. ......AtTa kKLSppPAaa lRLYRMGSGG
at1g13260 ~~~~~Mes.S SVDEStTSTg SIcetPAiTP aKkSS..vg. .nLYRMGS.G
at3g25730 ~~~~~MDamS SVDESSTtTD SI.......P arkSSsPAs. .lLYRMGS.G
 ntRAV_aa ~~~~~MegsS SiDEStTS.D SisiaPAist stL.pvmksp esLcRMGS.G 51                                            100
at1g50680 ~~mrLDdEpe nalVVssspk tvvaSgnvKY KGVVqQqNGh WGAQIYadHk
at1g51120 SvlsLtkrmk pteVttttkp aL..SnttKf KGVVqQqNGh WGAQIYadHr
at1g25560 SSVVLDSENG ....VEtESR KLPSS...KY KGVVPQPNGR WGAQIYEKHQ
at1g68840 SSVVLDpENG ....lEtESR KLPSS...KY KGVVPQPNGR WGAQIYEKHQ
at1g13260 SSVVLDSENG ....VEaESR KLPSS...KY KGVVPQPNGR WGAQIYEKHQ
at3g25730 tSVVLDSENG veveVEaESR KLPSS...rf KGVVPQPNGR WGAQIYEKHQ
 ntRAV_aa tSViiDaENG ....VEaESR KLPSS...rY eGVVPQPNGR WGAQIYEKHQ 101                                           150
at1g50680 RiWLGTFksa DEAAtAYDsA siklRsfDA. .NshrnfpWs tiTlnEpdFq
at1g51120 RiWLGTFksa hEAAaAYDsA siklRsfDA. .NshrnfpWs dfTlhEpdFq
at1g25560 RVWLGTFNEE eEAAssYDiA vrRFRGRDAV TNFKsqvdgn ...DaEsaFL
at1g68840 RVWLGTFNEq eEAARsYDiA AcRFRGRDAV vNFKnvle.. ...DgdlaFL
at1g13260 RVWLGTFNEE DEAARAYDVA vhRFRrRDAV TNFKdvkmdE ...D.EvdFL
at3g25730 RVWLGTFNEE DEAARAYDVA AhRFRGRDAV TNFKdttf.E ...e.EveFL
 ntRAV_aa RVWLGTFNEE nEAARAYDVA AqRFRGRDAV TNFKpllenE endDmEiaFL 151                                           200
at1g50680 Ncyttetvln MiRdgsYqhk frdflRiRSq IVasiN...i gGpKq..arg
at1g51120 ecytteavln MiRdgsYqhk frdflRiRSq IVaNiN...i vGsKqvlggg
at1g25560 dAHSKAEIVD MLRKHTYaDE fEQSrRk... .fvNGdGKRs .GLetatygN
at1g68840 eAHSKAEIVD MLRKHTYsDE LEQnnkrqlf lsvdaNGKRn .G..asttqN
at1g13260 NsHSKsEIVD MLRKHTYneE LEQSKRrR.. ...NGNGnmT rtLltsqlsN
at3g25730 NAHSKsEIVD MLRKHTYkeE LdQrKRnR.. ...dGNGKeT tafalasM..
 ntRAV_aa NsHSKAEIVD MLRKHTYiDE LEQSKknygf ...skdGKRT yctKdglMss
```

FIG. 6B

```
             201                                                           250
at1g50680   evnqEsdkCf  SctQLFqKel  TPSDVGKLNR  LVIPKkyAvK  ymPfiSaDQS
at1g51120   eGgqEsnkCf  SctQLFqKel  TPSDVGKLNR  LVIPKkyAvK  ymPfiSdDQS
at1g25560   DaV....l.R  aREvLFEKtV  TPSDVGKLNR  LVIPKQHAEK  HFPLPamtta
at1g68840   DkV....l.k  tREvLFEKAV  TPSDVGKLNR  LVIPKQHAEK  HFPLPS....
at1g13260   DGVsttGf.R  SaEaLFEKAV  TPSDVGKLNR  LVIPKhHAEK  HFPLP.....
at3g25730   ..VvmtGf.k  taElLFEKtV  TPSDVGKLNR  LVIPKhqAEK  HFPLP.....
ntRAV_aa    ffssvdkvtR  aREQLFEKAV  TPSDVGKLNR  LVIPKQHAEK  HFPL......

251                                                           300
at1g50680   EkEegeiVgs  VEDVevvFyD  ramrqWkFRY  cYWkSSQSfV  fTrGWnsFVK
at1g51120   EkEtse...G  VEDVevvFyD  ramrqWkFRY  cYWrSSQSfV  fTrGWngFVK
at1g25560   mgmNpsptKG  ...VLiNiED  rtGKVWRFRY  SYWNSSQSYV  LTKGWSRFVK
at1g68840   ..pspavtKG  ...VLiNFED  vNGKVWRFRY  SYWNSSQSYV  LTKGWSRFVK
at1g13260   ...ssnvSVKG ...VLLNFED  vNGKVWRFRY  SYWNSSQSYV  LTKGWSRFVK
at3g25730   lgnNnvSVKG  ...mLLNFED  vNGKVWRFRY  SYWNSSQSYV  LTKGWSRFVK
ntRAV_aa    ..qNgntsKG  ...VLLNFED  lNGKVWRFRY  SYWNSSQSYV  LTKGWSRFVK 301                                                           350
at1g50680   EKNLkekDVi  aFytcdvPnn  vktleqqrkN  FLMIDvhcfs  dnGsVVaEEV
at1g51120   EKNLkekDii  vFytcdvPnn  vktleqqSkt  FLMIDvhhfs  gnGfVVpEEV
at1g25560   EKNLrAGDVV  cFeRSTGPDr  QLYIhWKvR.  .....S....  spvQt.....
at1g68840   EKNLrAGDVV  tFeRSTGler  QLYIdWKvR.  .....SGpre  npvQV.....
at1g13260   EKNLrAGDVV  SFsRSnGqDq  QLYIgWKSR.  .....SGsdl  daGr......
at3g25730   EKrLcAGDii  SFkRSndqDq  kfflgWKSk.  .....SGldl  etGr......
ntRAV_aa    EKNLkAGDiV  SFqRSTGeDk  QLYIdfKaRN  atptiSptva  sqvQVqvpqV 351                                                           400
at1g50680   smTVhdssVq  vkKTEnLvsS  mledkeTKse  eNkGGFmlfG  vRiecp*~~~
at1g51120   nkTVheisde  emKTEtLftS  kvee.eTKse  ekkGGFmlfG  vRiq~~~~~~
at1g25560   .V.VRLFGVN  I.........  .FNvSneKpN  D.VaveCVGk  KRsRE.DdlF
at1g68840   .V.VRLFGVd  I.........  .FNvttvKpN  D.VvavC.GG  KRsRdVDdMF
at1g13260   .V.lRLFGVN  I.........  .speSsr..N  D.V....VGn  KRvndt.eMl
at3g25730   .V.mRLFGVd  I.........  .....sl..N  a.V....Vvv  KettEV.IMs
ntRAV_aa    qm.VRLFGVN  lcKvpavnnv  viNnnnnnnN  DNnmtsCsGG  KRriEmellt 401         416
at1g50680   ~~~~~~~~~~  ~~~~~~
at1g51120   ~~~~~~~~~~  ~~~~~~
at1g25560   SLgCSKKQa.  IIRiL*
at1g68840   aLRCSKKQa.  IINAL*
at1g13260   SLvCSKKQR.  IfhAs*
at3g25730   SLRC.KKQR.  vl*~~~
ntRAV_aa    fesCrKKQRv  IINAL~
```

FIG. 7A

~ - no corresponding sequence and beginning or end

. - Sequence Gaps

A - Identical Sequence a - Non-Identical Sequence ntRAV vs. Rice RAV-like peptides

```
                1                                                          50
   NP_909187.1  ~~~~~~~~~~ ~~~~mgvvsf ssts.sgAst attESggavr mspepVVavA
   NP_912459.1  ~~~~~~~~~~ meqeaamvvf scnsgsggss sttdS..... kqeeeeeeel
   NP_917049.1  MDSSSCLVDD TNSGgSStDK lRAlAAAAAE taP..LERMG SGASAVVDAA
   XP_475850.1  MDSSSCLVDD TNSGgSStDK lRAlAAAAAE taP..LERMG SGASAVVDAA
   NP_909194.1  MDStSCLlDD asSGaStgkK ....AAAAAa ska..LqRvG SGASAVmDAA
      ntRAV_aa  MegSSsides TtSdslSiap alststlpvm ksPESLcRMG SGtSvllD.A 51                                                         100
   NP_909187.1  aaaqqlpvvE Gvdsadevvt srpaAaaaqq SSrYKGVVPQ PNGRWGAQIY
   NP_912459.1  aameEdelih vvqaaelrlp s..sttatrP SSrYKGVVPQ PNGRWGAQIY
   NP_917049.1  EPGAEADSGS GgRVcGGGGG gaGGAGGKLP SSkfKGVVPQ PNGRWGAQIY
   XP_475850.1  EPGAEADSGS GgRVcGGGGG gaGGAGGKLP SSkfKGVVPQ PNGRWGAQIY
   NP_909194.1  EPGAEADS.. .......GGe rrGGgGGKLP SSkyKGVVPQ PNGRWGAQIY
      ntRAV_aa  EnGvEAeSr. .......... .......KLP SSrYeGVVPQ PNGRWGAQIY 101                                                         150
   NP_909187.1  ERHaRVWLGT FpdEeaAARA YDVAAlRyRG RDAaTNFpga A....asAAE
   NP_912459.1  ERHaRVWLGT FpdEeaAARA YDVAAlRFRG RDAVTNraPa AEg..asAgE
   NP_917049.1  ERHQRVWLGT FaGEddAARA YDVAAQRFRG RDAVTNFRPL AEADPdAAAE
   XP_475850.1  ERHQRVWLGT FaGEddAARA YDVAAQRFRG RDAVTNFRPL AEADPdAAAE
   NP_909194.1  ERHQRVWLGT FtGEaeAAPA YDVAAQRFRG RDAVTNFPPL AEsDPeAAvE
      ntRAV_aa  EkHQRVWLGT FneEneAARA YDVAAQRFRG RDAVTNFkPL lEneenddmE 151                                                         200
   NP_909187.1  LaFLAahSKA EiVDMLRKHT YaDELrQglR .......... ......rgrg
   NP_912459.1  LaFLAahSKA EVVDMLRKHT YdDELqQglR .......... ......r...
   NP_917049.1  LrFLAtrSKA EVVDMLRKHT YFDELAQSKR TFAASTPSAA tTTASLsNGH
   XP_475850.1  LrFLAtrSKA EVVDMLRKHT YFDELAQSKR TFAASTPSAA tTTASLsNGH
   NP_909194.1  LrFLAsrSKA EVVDMLRKHT YleELtQnKR aFAAlsPppp khpAS.....
      ntRAV_aa  laFLnshSKA EiVDMLRKHT YiDELeQSKk nygfSkd..g krTyctkdGl 201                                                         250
   NP_909187.1  mgaraqPTps W..AREpLFe KaVTPSDVGK LNRLVvPKQH AEKHFPL..r.
   NP_912459.1  .gSraqPTpr W..AREpLFe KaVTPSDVGK LNRLVvPKQq AErSFPfpL.
   NP_917049.1  lSSprSPfap .AAARdHLFd KtVTPSDVGK LNRLVlPKQH AEKHFPLQLP
```

Fig. 7B

```
XP_475850.1   lSSprSPfap .AAARdHLFd KtVTPSDVGK LNRLVIPKQH AEKHFPLQLP
NP_909194.1   .....SPTss .sAAREHLFd KtVTPSDVGK LNRLVIPKQH AEKHFPLQLP
   ntRAV_aa   mSSffSsvdk vtrAPEqLFe KaVTPSDVGK LNRLVIPKQH AEKHFPLQ..

251                                              300
NP_909187.1   ........RAA SSDsASAaat gKGVLLNFED geGKVWRFRY SYWNSSQSYV
NP_912459.1   ........Rrh SSDAA..... gKGVLLNFED gdGKVWRFRY SYWNSSQSYV
NP_917049.1   ........... .....SAGGe SKGVLLNFED AAGKVWRFRY SYWNSSQSYV
XP_475850.1   ........... .....SAGGe SKGVLLNFED AAGKVWRFRY SYWNSSQSYV
NP_909194.1   pptttssvAA aaDAAagGGd cKGVLLNFED AAGKVWkFRY SYWNSSQSYV
   ntRAV_aa   ........... ......nGnt SKGVLLNFED lnGKVWRFRY SYWNSSQSYV 301                                              350
NP_909187.1   LTKGWSRFVr EKGLrAGDti vFsRS..ayG pDKlLFIDCK k...N.nAAA
NP_912459.1   LTKGWSRFVr EKGLrpGDtV aFsRSAAawG teKhLlIDCK kmeRN.nlA.
NP_917049.1   LTKGWSRFVK EKGLHAGDvV GFYRSAAsAG DDgkLFIDCK l.vRsTgAA.
XP_475850.1   LTKGWSRFVK EKGLHAGDvV GFYRSAAsAG DDgkLFIDCK l.vRsTgAA.
NP_909194.1   LTKGWSRFVK EKGLHAGDaV GFYR...aAG knaqLFIDCK vrakpTtAAA
   ntRAV_aa   LTKGWSRFVK EKnLkAGDlV sFqR...stG eDKqLyIDfK ..aRNatpti 351                                              400
NP_909187.1   AtTTcAgder pttsgaeprv VRLFGVDiag gdcrkrerAv emgqevfllk
NP_912459.1   ...TvdddAr v........v VkLFGVDiag dktr~~~~~~ ~~~~~~~~~~
NP_917049.1   ....LASpAd QPAPSP.VKA VRLFGVDlLT APAPVEQMAG ....CKRARD
XP_475850.1   ....LASpAd QPAPSP.VKA VRLFGVDlLT APAPVEQMAG ....CKRARD
NP_909194.1   AaafLsavAa aaAPpPaVKA iRLFGVDlLT AaAPelQdAG gaamtKskRa
   ntRAV_aa   spTvasqvqv Qv...PqVgm VRLFGVnick vPAvnnvvin nnnnnnndnn 401                          439
NP_909187.1   rqcvvhqrtp Algalll~~~ ~~~~~~~~~~ ~~~~~~~~~~
NP_912459.1   ~~~~~~~~~~ ~~~~~~~~~~ ~~~~~~~~~~ ~~~~~~~~~~
NP_917049.1   lAATTPPQA. AAFKKQCIEL ALV~~~~~~~ ~~~~~~~~~~
XP_475850.1   lAATTPPQA. AAFKKQCIEL ALV~~~~~~~ ~~~~~~~~~~
NP_909194.1   mdAmaesQAh vvFKKQCIEL ALt~~~~~~~ ~~~~~~~~~~
   ntRAV_aa   mtscsgg... ....KrrIEm eLltfesork kqrviinal
```

FIG. 8

~ - no corresponding sequence and beginning or end

. - Sequence Gaps

A - Identical Sequence a - Non-Identical Sequence ntRAV vs Capsicum RAV-like peptide (gi|33320073|gb|AAQ05799.1)

```
                    1                                                          50
     ntRAV_aa  MEGsSSID.E  STTSDSLSIA  PaisTstlpv  mKsPESLCRM  GSGT.SVIID
     AAQ05799  MEGtSSIDqE  STTSDSLSIA  PmttT.....  .KpPESLCRM  GSGTsSVIID 51                                                         100
     ntRAV_aa  aENGVEAESR  KLPSSrYeGV  VPQPNGRWGA  QIYEKHQRVW  LGTFNEENEA
     AAQ05799  gENGVEAESR  KLPSSkYkGV  VPQPNGRWGA  QIYEKHQRVW  LGTFNEENEA 101                                                         150
     ntRAV_aa  ARAYDVAAQR  FRGRDAVTNF  KPLLENeE.n  DDmEIAFLNS  HSKAEIVDML
     AAQ05799  ARAYDVAAQR  FRGRDAVTNF  KPLLENqEsd  DDvEIAFLNS  HSKAEIVDML 151                                                         200
     ntRAV_aa  RKHTYIDELE  QSKKnyGfsK  DGkrtyctKD  GL...mSSFF.  ...ssvDKV.t
     AAQ05799  RKHTYIDELE  QSKKlfGytK  DGtmak.nKD  GLidiSSFFg  gggtiDKVnn 201                                                         250
     ntRAV_aa  raREQLFEKA  VTPSDVGKLN  RLVIPKQHAE  KHFPLQNGNt  SKGVLLNFED
     AAQ05799  kvREQLFEKA  VTPSDVGKLN  RLVIPKQHAE  KHFPLQNGNn  SKGVLLNFED 251                                                         300
     ntRAV_aa  LNGKVWRFRY  SYWNSSQSYV  LTKGWSRFVK  EKNLKAGDIV  SFQRSTgeDK
     AAQ05799  LNGKVWRFRY  SYWNSSQSYV  LTKGWSRFVK  EKNLKAGDIV  SFQRSTsgDK 301                                                         350
     ntRAV_aa  QLYIDFKARN  atPTisPtVa  sQV..QVQVP  qVQMvRLFGV  NICKvPAvnN
     AAQ05799  QLYIDFKARN  maPT.nPvVt  nQVqaQVQVP  rVQMmRLFGV  NICKiPAtiN 351                                     396
     ntRAV_aa  vVinNNNNNN  ndNNMtsCSG  GKRriEMELL  TFESCRKKQR  VIInAL
     AAQ05799  nVvdNNNNNN  ..NNManCSG  GKRmmEMELL  TFESCRKKQR  VIIdAL
```

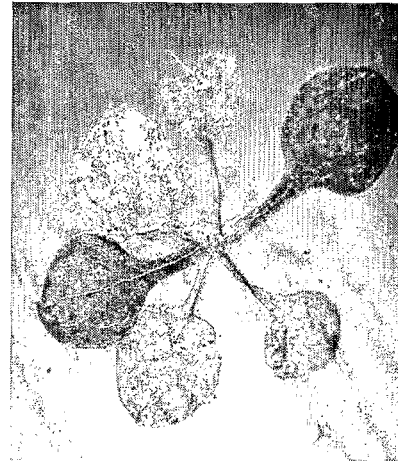
GUS silenced line L1
T-DNA insertion in RAV-2
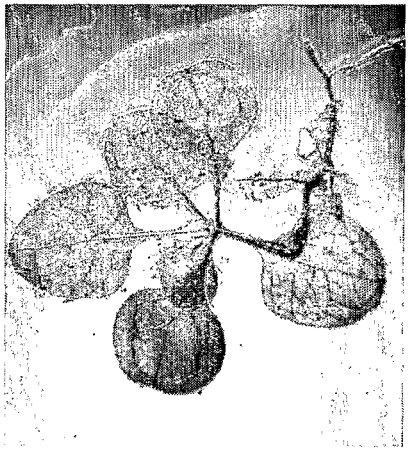
GUS silenced line L1
Wildtype for RAV-2
FIG. 9

FIG. 10A

AP2 domains ntRAV
63SRYEGVVPQPNGRWGAQIYEKHQRVWLGTFNEENEAARAYDVAAQRFRGRDAVTNFK119 csRAV  96.825
59SKYKGVVPQPNGRWGAQIYEKHQRVWLGTFNEENEAARAYDVAAQRFRGRDAVTNFK115

At3g25730  94.915
60SRFKGVVPQPNGRWGAQIYEKHQRVWLGTFNEEDEAARAYDVAAHRFRGRDAVTNFKD117

At1g25560  89.831
70SKYKGVVPQPNGRWGAQIYEKHQRVWLGTFNEEEEAASSYDIAVRRFRGRDAVTNFK126

At1g50680  60.714
27KYKGVVQQQNGHWGAQIYADHKRIWLGTFKSADEAATAYDSASIKLRSFDANSHRNFP84

At1g51120  64.815
45TKFKGVVQQQNGHWGAQIYADHRRIWLGTFKSAHEAAAAYDSASIKLRSFDANSHRNF102

At1g68840  91.525
63SKYKGVVPQPNGRWGAQIYEKHQRVWLGTFNEQEEAARSYDIAACRFRGRDAVVNFKN120

At1g13260  91.525
60SKYKGVVPQPNGRWGAQIYEKHQRVWLGTFNEEDEAARAYDVAVHRFRRRDAVTNFKD117 gi|34911404|ref|NP_917049.1  93.103
80SKFKGVVPQPNGRWGAQIYERHQRVWLGTFAGEDDAARAYDVAAQRFRGRDAVTNF135 gi|50932645|ref|XP_475850.1  93.103
80SKFKGVVPQPNGRWGAQIYERHQRVWLGTFAGEDDAARAYDVAAQRFRGRDAVTNF135 gi|34895690|ref|NP_909194.1  93.220
67SKYKGVVPQPNGRWGAQIYERHQRVWLGTFTGEAEAARAYDVAAQRFRGRDAVTNFR123 gi|34895676|ref|NP_909187.1  87.719
68RYKGVVPQPNGRWGAQIYERHARVWLGTFPDEEAAARAYDVAALRYRGRDAATNFP123 gi|34902226|ref|NP_912459.1  93.220
67YKGVVPQPNGRWGAQIYERHARVWLGTFPDEEAAARAYDVAALRFRGRDAVTN119

B3 Domains ntRAV
197LFEKAVTPSDVGKLNRLVIPKQHAEKHFPLQNGNTSKGVLLNFEDLNGKVWRFRYSYWNS256 csRAV  96.923
199LFEKAVTPSDVGKLNRLVIPKQHAEKHFPLQNGNNSKGVLLNFEDLNGKVWRFRYSYWNS258

FIG. 10B

At3g25730  44.444
182LFEKTVTPSDVGKLNRLVIPKHQAEKHFPLPLGNNNVSVKGMLLNFEDVNGKVWRFRYSY241

At1g25560  83.019
194LFEKTVTPSDVGKLNRLVIPKQHAEKHFPLPAMTTAMGMNPSPTKGVLINLEDRTGKVWR253

At1g50680  68.421
156LFQKELTPSDVGKLNRLVIPKKYAVKYMPFISADQSEKEEGEIVGSVEDVEVVFYDRAMR215

At1g51120  68.421
177LFQKELTPSDVGKLNRLVIPKKYAVKYMPFISDDQSEKETSEGVEDVEVVFYDRAMRQWK236

At1g68840  88.136
187LFEKAVTPSDVGKLNRLVIPKQHAEKHFPLPSPSPAVTKGVLINFEDVNGKVWRFRYSYW246

At1g13260  90.000
187LFEKAVTPSDVGKLNRLVIPKHHAEKHFPLPSSNVSVKGVLLNFEDVNGKVWRFRYSYWN246 gi|34911404|ref|NP_917049.1   89.655
215LFDKTVTPSDVGKLNRLVIPKQHAEKHFPLQLPSAGGESKGVLLNFEDAAGKVWRFRYSY274 gi|50932645|ref|XP_475850.1   89.655
215LFDKTVTPSDVGKLNRLVIPKQHAEKHFPLQLPSAGGESKGVLLNFEDAAGKVWRFRYSY274 gi|34895690|ref|NP_909194.1   96.875
192LFDKTVTPSDVGKLNRLVIPKQHAEKHFPLQLPPPTTTSSVAAAADAAAGGGDCKGVLLN251 gi|34895676|ref|NP_909187.1   86.538
181LFEKAVTPSDVGKLNRLVVPKQHAEKHFPLRRAASSDSASAAATGKGVLLNFEDGEGKVW240 gi|34902226|ref|NP_912459.1   82.143
177LFEKAVTPSDVGKLNRLVVPKQQAERHFPFPLRRHSSDAAGKGVLLNFEDGDGKVWRFRY236

SEQUENCE LISTING

```
<160> NUMBER OF SEQ ID NOS: 52

<210> SEQ ID NO 1
<211> LENGTH: 1154
<212> TYPE: DNA
<213> ORGANISM: Nicotiana tabacum

<400> SEQUENCE: 1
atggaaggta gcagcagcat agatgagagc acaactagtg actctctatc cattgctccg      60
gcaatatcca cgtcgacttt accggtgatg aagtcgccgg aaagtctttg ccgaatggga     120
agtggaacaa gtgtgataat agatgctgaa aatggagttg aagctgaatc aagaaaactc     180
ccatcttcaa ggtacgaagg tgtggtccca caaccaaatg gtcgatgggg cgcacaaatc     240
tatgaaaaac atcagcgagt ttggttaggt accttcaacg aagaaaatga agctgctagg     300
gcttatgacg tcgcggccca acgtttccgt ggccgcgacg ccgtcacaaa tttcaagccc     360
ttgcttgaaa atgaagaaaa tgatgatatg gaaattgctt tcttgaattc tcattcaaaa     420
gctgaaattg ttgatatgct tcgtaaacat acatatattg atgagcttga acaaagcaag     480
aaaaattatg gatttagtaa agatggtaaa agaacatatt gtactaaaga tgggctaatg     540
```

```
agttcatttt ttagtagtgt tgacaaagtc acaagagcgc gtgaacaact ctttgaaaaa    600
gctgttacac caagtgatgt tggaaaactt aataggcttg ttataccaaa acaacatgct    660
gaaaaacatt tccctttaca aaatggaaat acatcaaaag gggttttgtt aaattttgaa    720
gatttgaatg ggaaagtttg gagatttaga tattcctatt ggaatagtag ccaaagttat    780
gtgttgacaa aaggatggag tcgctttgtt aaggagaaaa atttgaaggc tggcgatatc    840
gtgagctttc agcgatccac aggcgaagat aagcaattgt acattgattt taaggcgaga    900
aatgcaacac ccacaattag tcctacagtt gctagtcaag ttcaggtgca agttcctcag    960
gtacaaatgg tgagattatt tggagttaac atatgcaaag taccagctgt aaataatgtt   1020
gttattaata ataataataa caacaataat gataataata tgactagttg cagtggtggc   1080
aaaaggagga tagagatgga gttgttgaca tttgagtcat gtagaaagaa acaaagggtt   1140
ataattaatg cctt                                                     1154
```

<210> SEQ ID NO 2
<211> LENGTH: 385
<212> TYPE: PRT
<213> ORGANISM: Nicotiana tabacum

<400> SEQUENCE: 2

```
Met Glu Gly Ser Ser Ser Ile Asp Glu Ser Thr Thr Ser Asp Ser Leu
1               5                   10                  15

Ser Ile Ala Pro Ala Ile Ser Thr Ser Thr Leu Pro Val Met Lys Ser
            20                  25                  30

Pro Glu Ser Leu Cys Arg Met Gly Ser Gly Thr Ser Val Ile Ile Asp
        35                  40                  45

Ala Glu Asn Gly Val Glu Ala Glu Ser Arg Lys Leu Pro Ser Ser Arg
    50                  55                  60

Tyr Glu Gly Val Val Pro Gln Pro Asn Gly Arg Trp Gly Ala Gln Ile
65                  70                  75                  80

Tyr Glu Lys His Gln Arg Val Trp Leu Gly Thr Phe Asn Glu Glu Asn
                85                  90                  95

Glu Ala Ala Arg Ala Tyr Asp Val Ala Ala Gln Arg Phe Arg Gly Arg
            100                 105                 110

Asp Ala Val Thr Asn Phe Lys Pro Leu Leu Glu Asn Glu Glu Asn Asp
        115                 120                 125

Asp Met Glu Ile Ala Phe Leu Asn Ser His Ser Lys Ala Glu Ile Val
    130                 135                 140

Asp Met Leu Arg Lys His Thr Tyr Ile Asp Glu Leu Glu Gln Ser Lys
145                 150                 155                 160

Lys Asn Tyr Gly Phe Ser Lys Asp Gly Lys Arg Thr Tyr Cys Thr Lys
                165                 170                 175

Asp Gly Leu Met Ser Ser Phe Phe Ser Ser Val Asp Lys Val Thr Arg
            180                 185                 190

Ala Arg Glu Gln Leu Phe Glu Lys Ala Val Thr Pro Ser Asp Val Gly
        195                 200                 205

Lys Leu Asn Arg Leu Val Ile Pro Lys Gln His Ala Glu Lys His Phe
    210                 215                 220

Pro Leu Gln Asn Gly Asn Thr Ser Lys Gly Val Leu Leu Asn Phe Glu
225                 230                 235                 240

Asp Leu Asn Gly Lys Val Trp Arg Phe Arg Tyr Ser Tyr Trp Asn Ser
                245                 250                 255

Ser Gln Ser Tyr Val Leu Thr Lys Gly Trp Ser Arg Phe Val Lys Glu
```

```
            260                 265                 270
Lys Asn Leu Lys Ala Gly Asp Ile Val Ser Phe Gln Arg Ser Thr Gly
            275                 280                 285

Glu Asp Lys Gln Leu Tyr Ile Asp Phe Lys Ala Arg Asn Ala Thr Pro
        290                 295                 300

Thr Ile Ser Pro Thr Val Ala Ser Gln Val Gln Val Gln Val Pro Gln
305                 310                 315                 320

Val Gln Met Val Arg Leu Phe Gly Val Asn Ile Cys Lys Val Pro Ala
                325                 330                 335

Val Asn Asn Val Val Ile Asn Asn Asn Asn Asn Asn Asn Asp Asn
            340                 345                 350

Asn Met Thr Ser Cys Ser Gly Gly Lys Arg Arg Ile Glu Met Glu Leu
        355                 360                 365

Leu Thr Phe Glu Ser Cys Arg Lys Lys Gln Arg Val Ile Ile Asn Ala
            370                 375                 380

Leu
385

<210> SEQ ID NO 3
<211> LENGTH: 344
<212> TYPE: PRT
<213> ORGANISM: Arabidopsis thaliana

<400> SEQUENCE: 3

Met Glu Ser Ser Ser Val Asp Glu Ser Thr Thr Ser Thr Gly Ser Ile
1               5                   10                  15

Cys Glu Thr Pro Ala Ile Thr Pro Ala Lys Lys Ser Ser Val Gly Asn
            20                  25                  30

Leu Tyr Arg Met Gly Ser Gly Ser Ser Val Val Leu Asp Ser Glu Asn
        35                  40                  45

Gly Val Glu Ala Glu Ser Arg Lys Leu Pro Ser Ser Lys Tyr Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Val His Arg Phe Arg Arg Arg Asp Ala Val
            100                 105                 110

Thr Asn Phe Lys Asp Val Lys Met Asp Glu Asp Glu Val Asp Phe Leu
        115                 120                 125

Asn Ser His Ser Lys Ser Glu Ile Val Asp Met Leu Arg Lys His Thr
    130                 135                 140

Tyr Asn Glu Glu Leu Glu Gln Ser Lys Arg Arg Arg Asn Gly Asn Gly
145                 150                 155                 160

Asn Met Thr Arg Thr Leu Leu Thr Ser Gly Leu Ser Asn Asp Gly Val
                165                 170                 175

Ser Thr Thr Gly Phe Arg Ser Ala Glu Ala Leu Phe Glu Lys Ala Val
            180                 185                 190

Thr Pro Ser Asp Val Gly Lys Leu Asn Arg Leu Val Ile Pro Lys His
        195                 200                 205

His Ala Glu Lys His Phe Pro Leu Pro Ser Ser Asn Val Ser Val Lys
    210                 215                 220

Gly Val Leu Leu Asn Phe Glu Asp Val Asn Gly Lys Val Trp Arg Phe
225                 230                 235                 240
```

```
Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Val Val
        260                 265                 270

Ser Phe Ser Arg Ser Asn Gly Gln Asp Gln Gln Leu Tyr Ile Gly Trp
            275                 280                 285

Lys Ser Arg Ser Gly Ser Asp Leu Asp Ala Gly Arg Val Leu Arg Leu
        290                 295                 300

Phe Gly Val Asn Ile Ser Pro Glu Ser Ser Arg Asn Asp Val Val Gly
305                 310                 315                 320

Asn Lys Arg Val Asn Asp Thr Glu Met Leu Ser Leu Val Cys Ser Lys
                325                 330                 335

Lys Gln Arg Ile Phe His Ala Ser
            340

<210> SEQ ID NO 4
<211> LENGTH: 352
<212> TYPE: PRT
<213> ORGANISM: Arabidopsis thaliana

<400> SEQUENCE: 4

Met Asp Ser Ser Cys Ile Asp Glu Ile Ser Ser Thr Ser Glu Ser
1               5                   10                  15

Phe Ser Ala Thr Thr Ala Lys Lys Leu Ser Pro Pro Ala Ala Ala
            20                  25                  30

Leu Arg Leu Tyr Arg Met Gly Ser Gly Ser Ser Val Val Leu Asp
        35                  40                  45

Pro Glu Asn Gly Leu Glu Thr Glu Ser Arg Lys Leu Pro Ser Ser Lys
50                  55                  60

Tyr Lys Gly Val Val Pro Gln Pro Asn Gly Arg Trp Gly Ala Gln Ile
65                  70                  75                  80

Tyr Glu Lys His Gln Arg Val Trp Leu Gly Thr Phe Asn Glu Gln Glu
                85                  90                  95

Glu Ala Ala Arg Ser Tyr Asp Ile Ala Ala Cys Arg Phe Arg Gly Arg
            100                 105                 110

Asp Ala Val Val Asn Phe Lys Asn Val Leu Glu Asp Gly Asp Leu Ala
        115                 120                 125

Phe Leu Glu Ala His Ser Lys Ala Glu Ile Val Asp Met Leu Arg Lys
130                 135                 140

His Thr Tyr Ala Asp Glu Leu Glu Gln Asn Asn Lys Arg Gln Leu Phe
145                 150                 155                 160

Leu Ser Val Asp Ala Asn Gly Lys Arg Asn Gly Ser Ser Thr Thr Gln
                165                 170                 175

Asn Asp Lys Val Leu Lys Thr Arg Glu Val Leu Phe Glu Lys Ala Val
            180                 185                 190

Thr Pro Ser Asp Val Gly Lys Leu Asn Arg Leu Val Ile Pro Lys Gln
        195                 200                 205

His Ala Glu Lys His Phe Pro Leu Pro Ser Pro Ser Pro Ala Val Thr
210                 215                 220

Lys Gly Val Leu Ile Asn Phe Glu Asp Val Asn Gly Lys Val Trp Arg
225                 230                 235                 240

Phe Arg Tyr Ser Tyr Trp Asn Ser Ser Gln Ser Tyr Val Leu Thr Lys
                245                 250                 255

Gly Trp Ser Arg Phe Val Lys Glu Lys Asn Leu Arg Ala Gly Asp Val
            260                 265                 270
```

```
Val Thr Phe Glu Arg Ser Thr Gly Leu Glu Arg Gln Leu Tyr Ile Asp
            275                 280                 285

Trp Lys Val Arg Ser Gly Pro Arg Glu Asn Pro Val Gln Val Val Val
290                 295                 300

Arg Leu Phe Gly Val Asp Ile Phe Asn Val Thr Thr Val Lys Pro Asn
305                 310                 315                 320

Asp Val Val Ala Val Cys Gly Gly Lys Arg Ser Arg Asp Val Asp Asp
            325                 330                 335

Met Phe Ala Leu Arg Cys Ser Lys Lys Gln Ala Ile Ile Asn Ala Leu
            340                 345                 350

<210> SEQ ID NO 5
<211> LENGTH: 352
<212> TYPE: PRT
<213> ORGANISM: Arabidopsis thaliana

<400> SEQUENCE: 5

Met Asp Glu Met Ser Asn Val Ala Lys Thr Thr Thr Glu Thr Ser Gly
1               5                   10                  15

Leu Thr Asp Ser Val Leu Ser Leu Thr Lys Arg Met Lys Pro Thr Glu
            20                  25                  30

Val Thr Thr Thr Thr Lys Pro Ala Leu Ser Asn Thr Thr Lys Phe Lys
        35                  40                  45

Gly Val Val Gln Gln Gln Asn Gly His Trp Gly Ala Gln Ile Tyr Ala
    50                  55                  60

Asp His Arg Arg Ile Trp Leu Gly Thr Phe Lys Ser Ala His Glu Ala
65                  70                  75                  80

Ala Ala Ala Tyr Asp Ser Ala Ser Ile Lys Leu Arg Ser Phe Asp Ala
                85                  90                  95

Asn Ser His Arg Asn Phe Pro Trp Ser Asp Phe Thr Leu His Glu Pro
            100                 105                 110

Asp Phe Gln Glu Cys Tyr Thr Thr Glu Ala Val Leu Asn Met Ile Arg
        115                 120                 125

Asp Gly Ser Tyr Gln His Lys Phe Arg Asp Phe Leu Arg Ile Arg Ser
    130                 135                 140

Gln Ile Val Ala Asn Ile Asn Ile Val Gly Ser Lys Gln Val Leu Gly
145                 150                 155                 160

Gly Gly Glu Gly Gly Gln Glu Ser Asn Lys Cys Phe Ser Cys Thr Gln
                165                 170                 175

Leu Phe Gln Lys Glu Leu Thr Pro Ser Asp Val Gly Lys Leu Asn Arg
            180                 185                 190

Leu Val Ile Pro Lys Lys Tyr Ala Val Lys Tyr Met Pro Phe Ile Ser
        195                 200                 205

Asp Asp Gln Ser Glu Lys Glu Thr Ser Glu Gly Val Glu Asp Val Glu
    210                 215                 220

Val Val Phe Tyr Asp Arg Ala Met Arg Gln Trp Lys Phe Arg Tyr Cys
225                 230                 235                 240

Tyr Trp Arg Ser Ser Gln Ser Phe Val Phe Thr Arg Gly Trp Asn Gly
                245                 250                 255

Phe Val Lys Glu Lys Asn Leu Lys Glu Lys Asp Ile Ile Val Phe Tyr
            260                 265                 270

Thr Cys Asp Val Pro Asn Asn Val Lys Thr Leu Glu Gly Gln Ser Lys
        275                 280                 285

Thr Phe Leu Met Ile Asp Val His His Phe Ser Gly Asn Gly Phe Val
```

```
            290                 295                 300
Val Pro Glu Glu Val Asn Lys Thr Val His Glu Ile Ser Asp Glu Glu
305                 310                 315                 320

Met Lys Thr Glu Thr Leu Phe Thr Ser Lys Val Glu Glu Thr Lys
                325                 330                 335

Ser Glu Glu Lys Lys Gly Gly Phe Met Leu Phe Gly Val Arg Ile Gln
                340                 345                 350

<210> SEQ ID NO 6
<211> LENGTH: 337
<212> TYPE: PRT
<213> ORGANISM: Arabidopsis thaliana

<400> SEQUENCE: 6

Met Arg Leu Asp Asp Glu Pro Glu Asn Ala Leu Val Val Ser Ser Ser
1               5                   10                  15

Pro Lys Thr Val Val Ala Ser Gly Asn Val Lys Tyr Lys Gly Val Val
                20                  25                  30

Gln Gln Gln Asn Gly His Trp Gly Ala Gln Ile Tyr Ala Asp His Lys
            35                  40                  45

Arg Ile Trp Leu Gly Thr Phe Lys Ser Ala Asp Glu Ala Ala Thr Ala
50                  55                  60

Tyr Asp Ser Ala Ser Ile Lys Leu Arg Ser Phe Asp Ala Asn Ser His
65                  70                  75                  80

Arg Asn Phe Pro Trp Ser Thr Ile Thr Leu Asn Glu Pro Asp Phe Gln
                85                  90                  95

Asn Cys Tyr Thr Thr Glu Thr Val Leu Asn Met Ile Arg Asp Gly Ser
            100                 105                 110

Tyr Gln His Lys Phe Arg Asp Phe Leu Arg Ile Arg Ser Gln Ile Val
        115                 120                 125

Ala Ser Ile Asn Ile Gly Gly Pro Lys Gln Ala Arg Gly Glu Val Asn
130                 135                 140

Gln Glu Ser Asp Lys Cys Phe Ser Cys Thr Gln Leu Phe Gln Lys Glu
145                 150                 155                 160

Leu Thr Pro Ser Asp Val Gly Lys Leu Asn Arg Leu Val Ile Pro Lys
                165                 170                 175

Lys Tyr Ala Val Lys Tyr Met Pro Phe Ile Ser Ala Asp Gln Ser Glu
            180                 185                 190

Lys Glu Glu Gly Glu Ile Val Gly Ser Val Glu Asp Val Glu Val Val
        195                 200                 205

Phe Tyr Asp Arg Ala Met Arg Gln Trp Lys Phe Arg Tyr Cys Tyr Trp
210                 215                 220

Lys Ser Ser Gln Ser Phe Val Phe Thr Arg Gly Trp Asn Ser Phe Val
225                 230                 235                 240

Lys Glu Lys Asn Leu Lys Glu Lys Asp Val Ile Ala Phe Tyr Thr Cys
                245                 250                 255

Asp Val Pro Asn Asn Val Lys Thr Leu Glu Gly Gln Arg Lys Asn Phe
            260                 265                 270

Leu Met Ile Asp Val His Cys Phe Ser Asp Asn Gly Ser Val Val Ala
        275                 280                 285

Glu Glu Val Ser Met Thr Val His Asp Ser Ser Val Gln Val Lys Lys
290                 295                 300

Thr Glu Asn Leu Val Ser Ser Met Leu Glu Asp Lys Glu Thr Lys Ser
305                 310                 315                 320
```

Glu Glu Asn Lys Gly Gly Phe Met Leu Phe Gly Val Arg Ile Glu Cys
                325                 330                 335

Pro

<210> SEQ ID NO 7
<211> LENGTH: 361
<212> TYPE: PRT
<213> ORGANISM: Arabidopsis thaliana

<400> SEQUENCE: 7

Met Glu Tyr Ser Cys Val Asp Asp Ser Ser Thr Thr Ser Glu Ser Leu
1               5                   10                  15

Ser Ile Ser Thr Thr Pro Lys Pro Thr Thr Thr Glu Lys Lys Leu
            20                  25                  30

Ser Ser Pro Pro Ala Thr Ser Met Arg Leu Tyr Arg Met Gly Ser Gly
            35                  40                  45

Gly Ser Ser Val Val Leu Asp Ser Glu Asn Gly Val Glu Thr Glu Ser
        50                  55                  60

Arg Lys Leu Pro Ser Ser Lys Tyr Lys Gly Val Val Pro Gln Pro Asn
65                  70                  75                  80

Gly Arg Trp Gly Ala Gln Ile Tyr Glu Lys His Gln Arg Val Trp Leu
                85                  90                  95

Gly Thr Phe Asn Glu Glu Glu Glu Ala Ala Ser Ser Tyr Asp Ile Ala
            100                 105                 110

Val Arg Arg Phe Arg Gly Arg Asp Ala Val Thr Asn Phe Lys Ser Gln
        115                 120                 125

Val Asp Gly Asn Asp Ala Glu Ser Ala Phe Leu Asp Ala His Ser Lys
    130                 135                 140

Ala Glu Ile Val Asp Met Leu Arg Lys His Thr Tyr Ala Asp Glu Phe
145                 150                 155                 160

Glu Gln Ser Arg Arg Lys Phe Val Asn Gly Asp Gly Lys Arg Ser Gly
                165                 170                 175

Leu Glu Thr Ala Thr Tyr Gly Asn Asp Ala Val Leu Arg Ala Arg Glu
            180                 185                 190

Val Leu Phe Glu Lys Thr Val Thr Pro Ser Asp Val Gly Lys Leu Asn
        195                 200                 205

Arg Leu Val Ile Pro Lys Gln His Ala Glu Lys His Phe Pro Leu Pro
    210                 215                 220

Ala Met Thr Thr Ala Met Gly Met Asn Pro Ser Pro Thr Lys Gly Val
225                 230                 235                 240

Leu Ile Asn Leu Glu Asp Arg Thr Gly Lys Val Trp Arg Phe Arg Tyr
                245                 250                 255

Ser Tyr Trp Asn Ser Ser Gln Ser Tyr Val Leu Thr Lys Gly Trp Ser
            260                 265                 270

Arg Phe Val Lys Glu Lys Asn Leu Arg Ala Gly Asp Val Val Cys Phe
        275                 280                 285

Glu Arg Ser Thr Gly Pro Asp Arg Gln Leu Tyr Ile His Trp Lys Val
    290                 295                 300

Arg Ser Ser Pro Val Gln Thr Val Val Arg Leu Phe Gly Val Asn Ile
305                 310                 315                 320

Phe Asn Val Ser Asn Glu Lys Pro Asn Asp Val Ala Val Glu Cys Val
                325                 330                 335

Gly Lys Lys Arg Ser Arg Glu Asp Leu Phe Ser Leu Gly Cys Ser
            340                 345                 350

```
Lys Lys Gln Ala Ile Ile Asn Ile Leu
        355                 360
```

<210> SEQ ID NO 8
<211> LENGTH: 333
<212> TYPE: PRT
<213> ORGANISM: Arabidopsis thaliana

<400> SEQUENCE: 8

```
Met Asp Ala Met Ser Ser Val Asp Glu Ser Thr Thr Thr Asp Ser
1               5                   10                  15

Ile Pro Ala Arg Lys Ser Ser Pro Ala Ser Leu Leu Tyr Arg Met
                20                  25                  30

Gly Ser Gly Thr Ser Val Val Leu Asp Ser Glu Asn Gly Val Glu Val
                35                  40                  45

Glu Val Glu Ala Glu Ser Arg Lys Leu Pro Ser Ser Arg Phe Lys Gly
        50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                    85                  90                  95

Arg Ala Tyr Asp Val Ala Ala His Arg Phe Arg Gly Arg Asp Ala Val
                100                 105                 110

Thr Asn Phe Lys Asp Thr Thr Phe Glu Glu Val Glu Phe Leu Asn
                115                 120                 125

Ala His Ser Lys Ser Glu Ile Val Asp Met Leu Arg Lys His Thr Tyr
        130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                    165                 170                 175

Lys Thr Ala Glu Leu Leu Phe Glu Lys Thr Val Thr Pro Ser Asp Val
                180                 185                 190

Gly Lys Leu Asn Arg Leu Val Ile Pro Lys His Gln Ala Glu Lys His
                195                 200                 205

Phe Pro Leu Pro Leu Gly Asn Asn Asn Val Ser Val Lys Gly Met Leu
        210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
                    245                 250                 255

Phe Val Lys Glu Lys Arg Leu Cys Ala Gly Asp Leu Ile Ser Phe Lys
                260                 265                 270

Arg Ser Asn Asp Gln Asp Gln Lys Phe Phe Ile Gly Trp Lys Ser Lys
        275                 280                 285

Ser Gly Leu Asp Leu Glu Thr Gly Arg Val Met Arg Leu Phe Gly Val
        290                 295                 300

Asp Ile Ser Leu Asn Ala Val Val Val Lys Glu Thr Thr Glu Val
305                 310                 315                 320

Leu Met Ser Ser Leu Arg Cys Lys Lys Gln Arg Val Leu
                325                 330
```

<210> SEQ ID NO 9
<211> LENGTH: 386
<212> TYPE: PRT
<213> ORGANISM: Capsicum sp.

<400> SEQUENCE: 9

```
Met Glu Gly Thr Ser Ser Ile Asp Gln Glu Ser Thr Thr Ser Asp Ser
1               5                   10                  15

Leu Ser Ile Ala Pro Met Thr Thr Lys Pro Pro Glu Ser Leu Cys
            20                  25                  30

Arg Met Gly Ser Gly Thr Ser Ser Val Ile Ile Asp Gly Glu Asn Gly
        35                  40                  45

Val Glu Ala Glu Ser Arg Lys Leu Pro Ser Ser Lys Tyr Lys Gly Val
    50                  55                  60

Val Pro Gln Pro Asn Gly Arg Trp Gly Ala Gln Ile Tyr Glu Lys His
65                  70                  75                  80

Gln Arg Val Trp Leu Gly Thr Phe Asn Glu Glu Asn Glu Ala Ala Arg
                85                  90                  95

Ala Tyr Asp Val Ala Ala Gln Arg Phe Arg Gly Arg Asp Ala Val Thr
            100                 105                 110

Asn Phe Lys Pro Leu Leu Glu Asn Gln Glu Ser Asp Asp Val Glu
            115                 120                 125

Ile Ala Phe Leu Asn Ser His Ser Lys Ala Glu Ile Val Asp Met Leu
130                 135                 140

Arg Lys His Thr Tyr Ile Asp Glu Leu Glu Gln Ser Lys Lys Leu Phe
145                 150                 155                 160

Gly Tyr Thr Lys Asp Gly Thr Met Ala Lys Asn Lys Asp Gly Leu Ile
                165                 170                 175

Asp Ile Ser Ser Phe Phe Gly Gly Gly Thr Ile Asp Lys Val Asn
            180                 185                 190

Asn Lys Val Arg Glu Gln Leu Phe Glu Lys Ala Val Thr Pro Ser Asp
        195                 200                 205

Val Gly Lys Leu Asn Arg Leu Val Ile Pro Lys Gln His Ala Glu Lys
    210                 215                 220

His Phe Pro Leu Gln Asn Gly Asn Asn Ser Lys Gly Val Leu Leu Asn
225                 230                 235                 240

Phe Glu Asp Leu Asn Gly Lys Val Trp Arg Phe Arg Tyr Ser Tyr Trp
                245                 250                 255

Asn Ser Ser Gln Ser Tyr Val Leu Thr Lys Gly Trp Ser Arg Phe Val
            260                 265                 270

Lys Glu Lys Asn Leu Lys Ala Gly Asp Ile Val Ser Phe Gln Arg Ser
        275                 280                 285

Thr Ser Gly Asp Lys Gln Leu Tyr Ile Asp Phe Lys Ala Arg Asn Met
    290                 295                 300

Ala Pro Thr Asn Pro Val Val Thr Asn Gln Val Gln Ala Gln Val Gln
305                 310                 315                 320

Val Pro Arg Val Gln Met Met Arg Leu Phe Gly Val Asn Ile Cys Lys
                325                 330                 335

Ile Pro Ala Thr Ile Asn Asn Val Asp Asn Asn Asn Asn Asn
            340                 345                 350

Asn Asn Met Ala Asn Cys Ser Gly Gly Lys Arg Met Met Glu Met Glu
        355                 360                 365

Leu Leu Thr Phe Glu Ser Cys Arg Lys Lys Gln Arg Val Ile Ile Asp
    370                 375                 380

Ala Leu
385
```

```
<210> SEQ ID NO 10
<211> LENGTH: 393
<212> TYPE: PRT
<213> ORGANISM: Oryza sativa

<400> SEQUENCE: 10
```

| | | | | | | | | | | | | | | |
|---|---|---|---|---|---|---|---|---|---|---|---|---|---|---|
| Met | Asp | Ser | Ser | Ser | Cys | Leu | Val | Asp | Asp | Thr | Asn | Ser | Gly | Gly | Ser |
| 1 | | | | 5 | | | | | 10 | | | | | 15 |

Ser Thr Asp Lys Leu Arg Ala Leu Ala Ala Ala Ala Glu Thr Ala
                20                  25                  30

Pro Leu Glu Arg Met Gly Ser Gly Ala Ser Ala Val Val Asp Ala Ala
            35                  40                  45

Glu Pro Gly Ala Glu Ala Asp Ser Gly Ser Gly Gly Arg Val Cys Gly
50                  55                  60

Gly Gly Gly Gly Ala Gly Gly Ala Gly Gly Lys Leu Pro Ser Ser
65                  70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
        115                 120                 125

Arg Asp Ala Val Thr Asn Phe Arg Pro Leu Ala Glu Ala Asp Pro Asp
130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Ser Pro Arg Ser Pro Phe Ala Pro
        195                 200                 205

Ala Ala Ala Arg Asp His Leu Phe Asp Lys Thr Val Thr Pro Ser Asp
210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Gly Leu His Ala Gly Asp Val Val Gly Phe
290                 295                 300

Tyr Arg Ser Ala Ala Ser Ala Gly Asp Asp Gly Lys Leu Phe Ile Asp
305                 310                 315                 320

Cys Lys Leu Val Arg Ser Thr Gly Ala Ala Leu Ala Ser Pro Ala Asp
                325                 330                 335

Gln Pro Ala Pro Ser Pro Val Lys Ala Val Arg Leu Phe Gly Val Asp
            340                 345                 350

Leu Leu Thr Ala Pro Ala Pro Val Glu Gln Met Ala Gly Cys Lys Arg
        355                 360                 365

Ala Arg Asp Leu Ala Ala Thr Thr Pro Pro Gln Ala Ala Ala Phe Lys
370                 375                 380

Lys Gln Cys Ile Glu Leu Ala Leu Val
385              390

<210> SEQ ID NO 11
<211> LENGTH: 393
<212> TYPE: PRT
<213> ORGANISM: Oryza sativa

<400> SEQUENCE: 11

Met Asp Ser Ser Ser Cys Leu Val Asp Asp Thr Asn Ser Gly Gly Ser
1               5                   10                  15

Ser Thr Asp Lys Leu Arg Ala Leu Ala Ala Ala Ala Glu Thr Ala
            20                  25                  30

Pro Leu Glu Arg Met Gly Ser Gly Ala Ser Ala Val Val Asp Ala Ala
            35                  40                  45

Glu Pro Gly Ala Glu Ala Asp Ser Gly Ser Gly Gly Arg Val Cys Gly
        50                  55                  60

Gly Gly Gly Gly Ala Gly Gly Ala Gly Lys Leu Pro Ser Ser
65                  70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
        115                 120                 125

Arg Asp Ala Val Thr Asn Phe Arg Pro Leu Ala Glu Ala Asp Pro Asp
130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Ser Pro Arg Ser Pro Phe Ala Pro
        195                 200                 205

Ala Ala Ala Arg Asp His Leu Phe Asp Lys Thr Val Thr Pro Ser Asp
210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Gly Leu His Ala Gly Asp Val Val Gly Phe
    290                 295                 300

Tyr Arg Ser Ala Ala Ser Ala Gly Asp Asp Gly Lys Leu Phe Ile Asp
305                 310                 315                 320

Cys Lys Leu Val Arg Ser Thr Gly Ala Ala Leu Ala Ser Pro Ala Asp
                325                 330                 335

Gln Pro Ala Pro Ser Pro Val Lys Ala Val Arg Leu Phe Gly Val Asp
            340                 345                 350

Leu Leu Thr Ala Pro Ala Pro Val Glu Gln Met Ala Gly Cys Lys Arg
        355                 360                 365

```
Ala Arg Asp Leu Ala Ala Thr Thr Pro Pro Gln Ala Ala Phe Lys
    370                 375                 380

Lys Gln Cys Ile Glu Leu Ala Leu Val
385                 390
```

<210> SEQ ID NO 12
<211> LENGTH: 394
<212> TYPE: PRT
<213> ORGANISM: Oryza sativa

<400> SEQUENCE: 12

```
Met Asp Ser Thr Ser Cys Leu Leu Asp Asp Ala Ser Ser Gly Ala Ser
1               5                   10                  15

Thr Gly Lys Lys Ala Ala Ala Ala Ala Ser Lys Ala Leu Gln Arg
                20                  25                  30

Val Gly Ser Gly Ala Ser Ala Val Met Asp Ala Ala Glu Pro Gly Ala
            35                  40                  45

Glu Ala Asp Ser Gly Gly Glu Arg Arg Gly Gly Gly Gly Lys Leu
    50                  55                  60

Pro Ser Ser Lys Tyr Lys Gly Val Val Pro Gln Pro Asn Gly Arg Trp
65                  70                  75                  80

Gly Ala Gln Ile Tyr Glu Arg His Gln Arg Val Trp Leu Gly Thr Phe
                85                  90                  95

Thr Gly Glu Ala Glu Ala Ala Arg Ala Tyr Asp Val Ala Ala Gln Arg
            100                 105                 110

Phe Arg Gly Arg Asp Ala Val Thr Asn Phe Arg Pro Leu Ala Glu Ser
        115                 120                 125

Asp Pro Glu Ala Ala Val Glu Leu Arg Phe Leu Ala Ser Arg Ser Lys
    130                 135                 140

Ala Glu Val Val Asp Met Leu Arg Lys His Thr Tyr Leu Glu Glu Leu
145                 150                 155                 160

Thr Gln Asn Lys Arg Ala Phe Ala Ala Ile Ser Pro Pro Pro Pro Lys
                165                 170                 175

His Pro Ala Ser Ser Pro Thr Ser Ser Ser Ala Ala Arg Glu His Leu
            180                 185                 190

Phe Asp Lys Thr Val Thr Pro Ser Asp Val Gly Lys Leu Asn Arg Leu
        195                 200                 205

Val Ile Pro Lys Gln His Ala Glu Lys His Phe Pro Leu Gln Leu Pro
    210                 215                 220

Pro Pro Thr Thr Thr Ser Ser Val Ala Ala Ala Asp Ala Ala Ala
225                 230                 235                 240

Gly Gly Gly Asp Cys Lys Gly Val Leu Leu Asn Phe Glu Asp Ala Ala
                245                 250                 255

Gly Lys Val Trp Lys Phe Arg Tyr Ser Tyr Trp Asn Ser Ser Gln Ser
            260                 265                 270

Tyr Val Leu Thr Lys Gly Trp Ser Arg Phe Val Lys Glu Lys Gly Leu
        275                 280                 285

His Ala Gly Asp Ala Val Gly Phe Tyr Arg Ala Ala Gly Lys Asn Ala
    290                 295                 300

Gln Leu Phe Ile Asp Cys Lys Val Arg Ala Lys Pro Thr Thr Ala Ala
305                 310                 315                 320

Ala Ala Ala Ala Phe Leu Ser Ala Val Ala Ala Ala Ala Pro Pro
                325                 330                 335

Pro Ala Val Lys Ala Ile Arg Leu Phe Gly Val Asp Leu Leu Thr Ala
```

```
            340                 345                 350
Ala Ala Pro Glu Leu Gln Asp Ala Gly Gly Ala Ala Met Thr Lys Ser
        355                 360                 365

Lys Arg Ala Met Asp Ala Met Ala Glu Ser Gln Ala His Val Val Phe
    370                 375                 380

Lys Lys Gln Cys Ile Glu Leu Ala Leu Thr
385                 390

<210> SEQ ID NO 13
<211> LENGTH: 365
<212> TYPE: PRT
<213> ORGANISM: Oryza sativa

<400> SEQUENCE: 13

Met Gly Val Val Ser Phe Ser Ser Thr Ser Gly Ala Ser Thr Ala
1               5                   10                  15

Thr Thr Glu Ser Gly Gly Ala Val Arg Met Ser Pro Glu Pro Val Val
            20                  25                  30

Ala Val Ala Ala Ala Ala Gln Gln Leu Pro Val Val Lys Gly Val Asp
        35                  40                  45

Ser Ala Asp Glu Val Val Thr Ser Arg Pro Ala Ala Ala Ala Gln
    50                  55                  60

Gln Ser Ser Arg Tyr Lys Gly Val Val Pro Gln Pro Asn Gly Arg Trp
65                  70                  75                  80

Gly Ala Gln Ile Tyr Glu Arg His Ala Arg Val Trp Leu Gly Thr Phe
                85                  90                  95

Pro Asp Glu Glu Ala Ala Arg Ala Tyr Asp Val Ala Ala Leu Arg
            100                 105                 110

Tyr Arg Gly Arg Asp Ala Ala Thr Asn Phe Pro Gly Ala Ala Ala Ser
        115                 120                 125

Ala Ala Glu Leu Ala Phe Leu Ala Ala His Ser Lys Ala Glu Ile Val
    130                 135                 140

Asp Met Leu Arg Lys His Thr Tyr Ala Asp Glu Leu Arg Gln Gly Leu
145                 150                 155                 160

Arg Arg Gly Arg Gly Met Gly Ala Arg Ala Gln Pro Thr Pro Ser Trp
                165                 170                 175

Ala Arg Glu Pro Leu Phe Glu Lys Ala Val Thr Pro Ser Asp Val Gly
            180                 185                 190

Lys Leu Asn Arg Leu Val Val Pro Lys Gln His Ala Glu Lys His Phe
        195                 200                 205

Pro Leu Arg Arg Ala Ala Ser Ser Asp Ser Ala Ser Ala Ala Ala Thr
    210                 215                 220

Gly Lys Gly Val Leu Leu Asn Phe Glu Asp Gly Glu Gly Lys Val Trp
225                 230                 235                 240

Arg Phe Arg Tyr Ser Tyr Trp Asn Ser Ser Gln Ser Tyr Val Leu Thr
                245                 250                 255

Lys Gly Trp Ser Arg Phe Val Arg Glu Lys Gly Leu Arg Ala Gly Asp
            260                 265                 270

Thr Ile Val Phe Ser Arg Ser Ala Tyr Gly Pro Asp Lys Leu Leu Phe
        275                 280                 285

Ile Asp Cys Lys Lys Asn Asn Ala Ala Ala Thr Thr Cys Ala
    290                 295                 300

Gly Asp Glu Arg Pro Thr Thr Ser Gly Ala Glu Pro Arg Val Val Arg
305                 310                 315                 320
```

Leu Phe Gly Val Asp Ile Ala Gly Gly Asp Cys Arg Lys Arg Glu Arg
                325                 330                 335

Ala Val Glu Met Gly Gln Glu Val Phe Leu Leu Lys Arg Gln Cys Val
            340                 345                 350

Val His Gln Arg Thr Pro Ala Leu Gly Ala Leu Leu Leu
        355                 360                 365

<210> SEQ ID NO 14
<211> LENGTH: 317
<212> TYPE: PRT
<213> ORGANISM: Oryza sativa

<400> SEQUENCE: 14

Met Glu Gln Glu Ala Ala Met Val Val Phe Ser Cys Asn Ser Gly Ser
1               5                   10                  15

Gly Gly Ser Ser Ser Thr Thr Asp Ser Lys Gln Glu Glu Glu Glu Glu
            20                  25                  30

Glu Glu Leu Ala Ala Met Glu Glu Asp Glu Leu Ile His Val Val Gln
        35                  40                  45

Ala Ala Glu Leu Arg Leu Pro Ser Ser Thr Thr Ala Thr Arg Pro Ser
    50                  55                  60

Ser Arg Tyr Lys Gly Val Val Pro Gln Pro Asn Gly Arg Trp Gly Ala
65                  70                  75                  80

Gln Ile Tyr Glu Arg His Ala Arg Val Trp Leu Gly Thr Phe Pro Asp
                85                  90                  95

Glu Glu Ala Ala Ala Arg Ala Tyr Asp Val Ala Ala Leu Arg Phe Arg
            100                 105                 110

Gly Arg Asp Ala Val Thr Asn Arg Ala Pro Ala Ala Glu Gly Ala Ser
        115                 120                 125

Ala Gly Glu Leu Ala Phe Leu Ala His Ser Lys Ala Glu Val Val
    130                 135                 140

Asp Met Leu Arg Lys His Thr Tyr Asp Glu Leu Gln Gln Gly Leu
145                 150                 155                 160

Arg Arg Gly Ser Arg Ala Gln Pro Thr Pro Arg Trp Ala Arg Glu Pro
                165                 170                 175

Leu Phe Glu Lys Ala Val Thr Pro Ser Asp Val Gly Lys Leu Asn Arg
            180                 185                 190

Leu Val Val Pro Lys Gln Gln Ala Glu Arg His Phe Pro Phe Pro Leu
        195                 200                 205

Arg Arg His Ser Ser Asp Ala Ala Gly Lys Gly Val Leu Leu Asn Phe
    210                 215                 220

Glu Asp Gly Asp Gly Lys Val Trp Arg Phe Arg Tyr Ser Tyr Trp Asn
225                 230                 235                 240

Ser Ser Gln Ser Tyr Val Leu Thr Lys Gly Trp Ser Arg Phe Val Arg
                245                 250                 255

Glu Lys Gly Leu Arg Pro Gly Asp Thr Val Ala Phe Ser Arg Ser Ala
            260                 265                 270

Ala Ala Trp Gly Thr Glu Lys His Leu Leu Ile Asp Cys Lys Lys Met
        275                 280                 285

Glu Arg Asn Asn Leu Ala Thr Val Asp Asp Ala Arg Val Val Val
    290                 295                 300

Lys Leu Phe Gly Val Asp Ile Ala Gly Asp Lys Thr Arg
305                 310                 315

<210> SEQ ID NO 15

```
<211> LENGTH: 1035
<212> TYPE: DNA
<213> ORGANISM: Arabidopsis thaliana

<400> SEQUENCE: 15
atggaatcga gtagcgttga tgagagtact acaagtacag gttccatctg tgaaaccccg        60
gcgataactc cggcgaaaaa gtcgtcggta ggtaacttat acaggatggg aagcggatca       120
agcgttgtgt tagattcaga gaacggcgta aagctgaat ctaggaagct tccgtcgtca        180
aaatacaaag gtgtggtgcc acaaccaaac ggaagatggg gagctcagat ttacgagaaa       240
caccagcgcg tgtggctcgg acattcaac gaagaagacg aagccgctcg tgcctacgac        300
gtcgcggttc acaggttccg tcgccgtgac gccgtcacaa atttcaaaga cgtgaagatg       360
gacgaagacg aggtcgattt cttgaattct cattcgaaat ctgagatcgt tgatatgttg       420
aggaaacata cttataacga agagttagag cagagtaaac ggcgtcgtaa tggtaacgga       480
aacatgacta ggacgttgtt aacgtcgggg ttgagtaatg atggtgtttc tacgacgggg       540
tttagatcgg cggaggcact gtttgagaaa gcggtaacgc caagcgacgt tgggaagcta       600
aaccgtttgg ttataccgaa acatcacgca gagaaacatt ttccgttacc gtcaagtaac       660
gtttccgtga aaggagtgtt gttgaacttt gaggacgtta acgggaaagt gtggaggttc       720
cgttactcgt attggaacag tagtcagagt tatgttttga ctaaaggttg gagcaggttc       780
gttaaggaga gaatctacg tgctggtgac gtggttagtt tcagtagatc taacggtcag        840
gatcaacagt tgtacattgg gtggaagtcg agatccgggt cagatttaga tgcgggtcgg       900
gttttgagat tgttcggagt taacatttca ccggagagtt caagaaacga cgtcgtagga       960
aacaaaagag tgaacgatac tgagatgtta tcgttggtgt gtagcaagaa gcaacgcatc      1020
tttcacgcct cgtaa                                                       1035

<210> SEQ ID NO 16
<211> LENGTH: 1059
<212> TYPE: DNA
<213> ORGANISM: Arabidopsis thaliana

<400> SEQUENCE: 16
atggattcta gttgcataga cgagataagt tcctccactt cagaatcttt ctccgccacc        60
accgccaaga agctctctcc tcctcccgcg gcggcgttac gcctctaccg gatgggaagc       120
ggcgggagca gcgtcgtgtt ggatcccgag aacggcctag agacggagtc acgaaagcta       180
ccatcttcaa aatacaaagg tgttgttcct cagcctaacg gaagatgggg agctcagatc       240
tacgagaagc accaacgagt atggctcggg actttcaacg agcaagaaga agctgctcgt       300
tcctacgaca tcgcagcttg tagattccgt ggccgcgacg ccgtcgtcaa cttcaagaac       360
gttctggaag acggcgattt agcttttctt gaagctcact caaaggccga gatcgtcgac       420
atgttgagaa aacacactta cgccgacgag cttgaacaga caataaacg gcagttgttt        480
ctctccgtcg acgctaacgg aaaacgtaac ggatcgagta ctactcaaaa cgacaaagtt       540
ttaaagacgc gtgaagttct tttcgagaag gctgttacac ctagcgacgt tgggaagcta       600
aaccgtctcg tgatacctaa acaacacgcc gagaaacact ttccgttacc gtcaccgtca       660
ccggcagtga ctaaaggagt tttgatcaac ttcgaagacg ttaacggtaa agtgtggagg       720
ttccgttact catactggaa cagtagtcaa agttacgtgt tgaccaaggg atggagtcga       780
ttcgtcaagg agaagaatct tcgagccggt gatgttgtta ctttcgagag atcgaccgga       840
ctagagcggc agttatatat tgattggaaa gttcggtctg gtccgagaga aaacccggtt       900
```

```
caggtggtgg ttcggctttt cggagttgat atctttaatg tgaccaccgt gaagccaaac      960
gacgtcgtgg ccgtttgcgg tggaaagaga tctcgagatg ttgatgatat gtttgcgtta     1020
cggtgttcca agaagcaggc gataatcaat gctttgtga                            1059
```

<210> SEQ ID NO 17
<211> LENGTH: 1059
<212> TYPE: DNA
<213> ORGANISM: Arabidopsis thaliana

<400> SEQUENCE: 17

```
atggacgaga tgagcaatgt agccaagaca acgacagaga cttcaggctt aactgactct       60
gtcttgagcc tcacgaaacg catgaaacct actgaggtta cgaccaccac aaaacctgcc      120
ttgtccaaca cgacgaaatt caaaggagtt gttcagcaac agaacggtca ttggggtgct      180
cagatttacg cagaccatcg aaggatttgg cttggaactt caaatccgc tcatgaagcc      240 gctgctgctt acgatagcgc atcgattaag cttcgaagct ttgatgctaa ctcgcaccgg      300
aacttccctt ggtctgattt tacccctccat gaaccggact tcaagagtg ctacacgaca      360 gaagctgtgt tgaacatgat cagagacggt tcttatcaac acaagttcag agattttctc      420
agaatccggt ctcagattgt tgcgaatatc aacatcgtgg gatcaaaaca agtcttagga      480
ggaggagaag gtggtcaaga atcgaacaag tgtttctcgt gcacgcagct ttttcagaaa      540
gaactgacac cgagcgatgt agggaaactg aataggcttg tgatacctaa gaagtatgca      600
gtgaagtata tgccttcat aagcgatgat caaagcgaga agagacgag tgaaggagta      660 gaagatgtgg aggttgtctt ttacgacaga gcaatgagac aatggaagtt taggtattgt      720
tactggagaa gtagccagag cttgtcttc accagaggat ggaatggttt cgtgaaggag      780
aagaatctca aggagaaaga tattattgtc ttttacactt gcgatgtccc caacaatgtg      840
aagacattag aaggccaaag caagaccttc ttgatgattg atgttcatca cttttcaggc      900
aacggtttcg tggttcccga ggaagtaaac aagacggttc atgagatttc tgatgaagag      960
atgaaaacag aaaccctctt tacctcgaag gtagaagaag aaaccaaatc agaggagaag     1020
aaaggagggt ttatgctgtt tggtgttagg atccaatag                            1059
```

<210> SEQ ID NO 18
<211> LENGTH: 1014
<212> TYPE: DNA
<213> ORGANISM: Arabidopsis thaliana

<400> SEQUENCE: 18

```
atgagacttg atgacgaacc agaaaacgcc ctagtggttt cgtcttcacc aaagacggtt       60
gtggcttctg gcaatgtcaa gtacaaagga gtcgttcagc aacagaacgg tcattggggt      120
gcccagattt acgcagacca caaaaggatt tggcttggaa ctttcaaatc cgctgatgaa      180
gccgccacgg cttacgatag tgcatctatc aaactccgaa gctttgacgc taactcgcac      240
cggaacttcc cttggtctac aatcactctc aacgaaccag actttcaaaa ttgctacaca      300
acagagactg tgttgaacat gatcagagac ggttcgtacc aacacaaatt cagagatttt      360
ctcagaatca gatctcagat tgttgcgagt atcaacatcg ggggaccaaa acaagcccga      420
ggagaagtga atcaagaatc agacaagtgt tttctcttgca cacagctttt tcagaaggaa      480
ttgacaccga gcgatgtagg gaaactaaat aggcttgtga tacctaaaaa gtatgcagtg      540
aagtatatgc ctttcataag cgctgatcaa agcgagaaag aagagggtga aatagtagga      600
```

| | |
|---|---|
| tctgtggaag atgtggaggt tgtgttttac gacagagcaa tgagacaatg gaagtttagg | 660 |
| tattgttact ggaaaagtag ccagagcttt gtcttcacca gaggatggaa tagtttcgtg | 720 |
| aaggagaaga atctcaagga gaaggatgtt attgccttct acacttgcga tgtcccgaac | 780 |
| aatgtgaaga cattagaagg tcaaagaaag aacttcttga tgatcgatgt tcattgcttt | 840 |
| tcagacaacg gttccgtggt agctgaggaa gtaagtatga cggttcatga cagttcagtg | 900 |
| caagtaaaga aaacagaaaa cttggttagc tccatgttag aagataaaga aaccaaatca | 960 |
| gaggagaaca aaggagggtt tatgctgttt ggtgtaagga tcgaatgtcc ttag | 1014 |

<210> SEQ ID NO 19
<211> LENGTH: 1086
<212> TYPE: DNA
<213> ORGANISM: Arabidopsis thaliana

<400> SEQUENCE: 19

| | |
|---|---|
| atggaataca gctgtgtaga cgacagtagt acaacgtcag aatctctctc catctctact | 60 |
| actccaaagc cgacaacgac gacggagaag aaactctctt ctccgccggc gacgtcgatg | 120 |
| cgtctctaca gaatgggaag cggcggaagc agcgtcgttt tggattcaga aacggcgtc | 180 |
| gagaccgagt cacgtaagct tccttcgtcg aaatataaag gcgttgtgcc tcagcctaac | 240 |
| ggaagatggg gagctcagat ttacgagaag catcagcgag tttggctcgg tactttcaac | 300 |
| gaggaagaag aagctgcgtc ttcttacgac atcgccgtga ggagattccg cggccgcgac | 360 |
| gccgtcacta acttcaaatc tcaagttgat ggaaacgacg ccgaatcggc ttttcttgac | 420 |
| gctcattcta aagctgagat cgtggatatg ttgaggaaac acacttacgc cgatgagttt | 480 |
| gagcagagta gacggaagtt tgttaacggc gacggaaaac gctctgggtt ggagacggcg | 540 |
| acgtacggaa acgacgctgt tttgagagcg cgtgaggttt tgttcgagaa gactgttacg | 600 |
| ccgagcgacg tcgggaagct gaaccgttta gtgataccga acaacacgc ggagaagcat | 660 |
| tttccgttac cggcgatgac gacggcgatg gggatgaatc cgtctccgac gaaaggcgtt | 720 |
| tgattaact tggaagatag aacagggaaa gtgtggcggt tccgttacag ttactggaac | 780 |
| agcagtcaaa gttacgtgtt gaccaagggc tggagccggt tcgttaaaga gaagaatctt | 840 |
| cgagccggtg atgtggtttg tttcgagaga tcaaccggac cagaccggca attgtatatc | 900 |
| cactggaaag tccggtctag tccggttcag actgtggtta ggctattcgg agtcaacatt | 960 |
| ttcaatgtga gtaacgagaa accaaacgac gtcgcagtag agtgtgttgg caagaagaga | 1020 |
| tctcgggaag atgatttgtt ttcgttaggg tgttccaaga agcaggcgat tatcaacatc | 1080 |
| ttgtga | 1086 |

<210> SEQ ID NO 20
<211> LENGTH: 1002
<212> TYPE: DNA
<213> ORGANISM: Arabidopsis thaliana

<400> SEQUENCE: 20

| | |
|---|---|
| atggatgcca tgagtagcgt agacgagagc tctacaacta cagattccat tccggcgaga | 60 |
| aagtcatcgt ctccggcgag tttactatat agaatgggaa gcggaacaag cgtggtactt | 120 |
| gattcagaga acggtgtcga agtcgaagtc gaagccgaat caagaaagct tccttcttca | 180 |
| agattcaaag gtgttgttcc tcaaccaaat ggaagatggg gagctcagat ttacgagaaa | 240 |
| catcaacgcg tgtggcttgg tactttcaac gaggaagacg aagcagctcg tgcttacgac | 300 |
| gtcgcggctc accgtttccg tggccgcgat gccgttacta atttcaaaga cacgacgttc | 360 |

-continued

```
gaagaagagg ttgagttctt aaacgcgcat tcgaaatcag agatcgtaga tatgttgaga      420
aaacacactt acaaagaaga gttagaccaa aggaaacgta accgtgacgg taacggaaaa      480
gagacgacgg cgtttgcttt ggcttcgatg gtggttatga cggggtttaa aacggcggag      540
ttactgtttg agaaaacggt aacgccaagt gacgtcggga aactaaaccg tttagttata      600
ccaaaacacc aagcggagaa acattttccg ttaccgttag gtaataataa cgtctccgtt      660
aaaggtatgc tgttgaattt cgaagacgtt aacgggaaaa tgtggaggtt ccgttactct      720
tattggaata gtagtcaaag ttatgtgttg accaaaggtt ggagtagatt cgttaaagag      780
aagagacttt gtgctggtga tttgatcagt tttaaaagat ccaacgatca agatcaaaaa      840
ttctttatcg ggtggaaatc gaaatccggg ttggatctag agacgggtcg ggttatgaga      900
ttgtttgggg ttgatatttc tttaaacgcc gtcgttgtag tgaaggaaac aacggaggtg      960
ttaatgtcgt cgttaaggtg taagaagcaa cgagttttgt aa                       1002
```

<210> SEQ ID NO 21
<211> LENGTH: 1161
<212> TYPE: DNA
<213> ORGANISM: Capsicum sp.

<400> SEQUENCE: 21

```
atggaaggaa ctagtagcat agatcaagag agcactacta gtgactctct ctccattgct       60
ccgatgacga cgaccaagcc gccggagagt ctttgtagga tggggagtgg aacaagtagt      120
gtgataattg atggtgaaaa tggtgttgaa gctgaatcaa gaaaactccc atcttcaaaa      180
tacaaaggtg tggtccctca accaaatgga cgttggggtg cacaaatcta tgaaaagcat      240
caaagggttt ggttaggcac attcaacgag gagaatgaag ccgccagggc atatgacgtc      300
gcggcccaga ggttcagggg ccgcgacgct gttactaatt tcaaacccct tacttgagaat      360 caagaaagtg atgatgatgt ggaaatcgct ttcttgaact cgcattccaa ggcggagatt      420
gttgacatgt tacgtaaaca tacgtatatc gatgagttag aacaaagtaa gaaattattt      480
ggatatacta aagatggtac catggcaaaa aataaagatg gacttattga tataagttca      540
ttttttggtg gtggtggtac tattgataaa gtcaacaaca aagttcgtga acagttattt      600
gaaaaagctg ttaccccaag tgatgttggt aaattaaata ggcttgtgat accaaaacaa      660
catgctgaaa acattttcc attacaaaat ggaataact cgaaagggt tttgttgaat       720 ttcgaagatt taaatggtaa agtttggaga tttagatatt cgtattggaa tagtagtcaa      780
agttatgttt taaccaaagg atggagtcgt ttcgtaaaag aaaaaaactt gaaggccggt      840
gatattgtga gttttcagcg atctacaagt ggagataagc aattgtacat cgattttaag      900
gctaggaata tggccccac aaatccggtc gttactaatc aagttcaagc tcaggttcaa      960
gttccgcgag tacaaatgat gagattattc ggagttaata tatgcaagat acccgctacg     1020
ataaataatg ttgttgataa taataacaac aacaacaata atatggctaa ttgtagtggg     1080
ggcaaaagga tgatggagat ggaattgttg acatttgagt catgtaggaa gaaacaaagg     1140
gtgattattg atgccttgta a                                               1161
```

<210> SEQ ID NO 22
<211> LENGTH: 1182
<212> TYPE: DNA
<213> ORGANISM: Oryza sativa
<400> SEQUENCE: 22

```
atggacagct ccagctgcct ggtggatgat accaacagcg gcggctcgtc cacggacaag      60
ctgagggcgt tggccgccgc ggcggcggag acggcgccgc tggagcgcat ggggagcggg     120
gcgagcgcgg tggtggacgc ggccgagcct ggcgcggagg cggactccgg gtccggggga     180
cgtgtgtgcg gcggcggcgg cggcggtgcc ggcggtgcgg agggaagct  gccgtcgtcc     240
aagttcaagg gcgtcgtgcc gcagcccaac gggaggtggg gcgcgcagat ctacgagcgg     300
caccagcggg tgtggctcgg cacgttcgcc ggggaggacg acgccgcgcg cgcctacgac     360
gtcgccgcgc agcgcttccg cggccgcgac gccgtcacca acttccgccc gctcgccgag     420
gccgacccgg acgccgccgc cgagcttcgc ttcctcgcca cgcgctccaa ggccgaggtc     480
gtcgacatgc tccgcaagca cacctacttc gacgagctcg cgcagagcaa gcgcaccttc     540
gccgcctcca cgccgtcggc cgcgaccacc accgcctccc tctccaacgg ccacctctcg     600
tcgcccgct  cccccttcgc gcccgccgcg gcgcgcgacc acctgttcga caagacggtc     660
accccgagcg acgtgggcaa gctgaacagg ctcgtcatac cgaagcagca cgccgagaag     720
cacttcccgc tacagctccc gtccgccggc ggcgagagca agggtgtcct cctcaacttc     780
gaggacgccg ccggcaaggt gtggcggttc cggtactcgt actggaacag cagccagagc     840
tacgtgctaa ccaagggctg gagccgcttc gtcaaggaga agggtctcca cgccggcgac     900
gtcgtcggct tctaccgctc cgccgccagt gccggcgacg acggcaagct cttcatcgac     960
tgcaagttag tacggtcgac cggcgccgcc ctcgcgtcgc ccgctgatca gccagcgccg    1020
tcgccggtga aggccgtcag gctcttcggc gtggacctgc tcacggcgcc ggcgccggtc    1080
gaacagatgg ccgggtgcaa gagagccagg gacttggcgg cgacgacgcc tccacaagcg    1140
gcggcgttca agaagcaatg catagagctg gcactagtat ag                       1182

<210> SEQ ID NO 23
<211> LENGTH: 1185
<212> TYPE: DNA
<213> ORGANISM: Oryza sativa

<400> SEQUENCE: 23
atggacagca cgagctgtct cttggacgac gcgagcagcg gcgcgtccac gggcaagaag      60
gcggcggcgg cggcggcgtc gaaggcgctg cagcgcgtgg gcagcggcgc cagcgcggtg     120
atggacgcgc ccgagcctgg cgccgaggcg gactcgggcg gcgagcggcg cggcggcggc     180
ggcgggaagc tgccgtcgtc caagtacaag ggcgtggtgc cgcaaccgaa cgggcggtgg     240
ggcgcgcaga tatacgagcg gcaccagcgg gtgtggctcg gcacgttcac cggcgaggcg     300
gaggcggcgc gcgcctacga cgtggcggcg cagcggttcc gcggccgcga cgccgtcacc     360
aacttccgcc cgctcgccga gtccgacccg gaggccgccg tcgagctccg cttcctcgcg     420
tcccgctcca aggccgaggt cgtcgacatg ctccgcaagc acacctacct cgaggagctc     480
acgcagaaca gcgcgccctt cgccgccatc tccccgccgc ccccaagca ccccgcctcc     540
tctccgacgt cctcctccgc cgcgcgcgag cacctgttcg acaagacggt gacgcccagc     600
gacgtcggga agctgaaccg gctggtgatc cccaagcagc acgccgagaa gcacttcccg     660
ctccagctcc ctccccctac cacaacctcc tccgtcgccg ccgccgccga cgccgccgcc     720
ggcggcggcg attgcaaggg cgtcctcctc aacttcgagg acgccgccgg gaaggtgtgg    780
aaattccggt actcctactg gaacagcagc cagagctacg tgctcaccaa ggggtggagc     840
cgcttcgtca aggagaaggg gctccacgcc ggcgacgccg tcggcttcta ccgcgccgcc     900
ggtaagaacg cgcagctctt catcgactgc aaggtccggg caaaacccac caccgccgcc     960
```

| | |
|---|---:|
| gccgccgccg ccttcctcag cgcggtggcc gccgccgccg cgccgccacc cgccgtgaag | 1020 |
| gctatcaggc tgttcggtgt cgacctgctc acggcggcgg cgccggagct gcaggacgcc | 1080 |
| ggcggcgccg ccatgaccaa gagcaagaga gccatggacg ccatggctga gtcacaagca | 1140 |
| cacgtggttt ttaagaagca atgcatagag cttgcgctaa cctag | 1185 |

<210> SEQ ID NO 24
<211> LENGTH: 1098
<212> TYPE: DNA
<213> ORGANISM: Oryza sativa

<400> SEQUENCE: 24

| | |
|---|---:|
| atgggggtgg tcagcttctc ctcgacttcc tccggcgcgt ccacggccac caccgagtcc | 60 |
| ggcggcgccg tgcggatgtc gccggagccg tggtggcgg tggcggcggc ggctcaacag | 120 |
| ctaccggtgg tgaagggagt tgactcggcg gatgaggtgg tgacgtcgag gccggcggcg | 180 |
| gcggcggcgc agcagtcgtc gcggtacaag ggggtggtgc cgcagccgaa cgggaggtgg | 240 |
| ggggcgcaga tctacgagcg gcacgcgcgg gtgtggctcg gacgttccc cgacgaggag | 300 |
| gcggcggcgc gggcctacga cgtggcgcg ctccggtacc gggggcgcga cgcggccacc | 360 |
| aacttccccg gggccgcggc gtcggccgcc gagctcgcgt tcctcgccgc gcactccaag | 420 |
| gccgagatcg tcgacatgct ccggaagcac acctacgccg acgagctccg ccaggggctc | 480 |
| cgccgcggcc gcggcatggg cgcccgcgcc cagcccacgc cgtcgtgggc gcgcgagccg | 540 |
| ctgttcgaga aggccgtgac gcccagcgac gtcggcaagc tcaaccgcct cgtggtgccc | 600 |
| aagcagcacg ccgagaagca cttcccgctc cgccgcgcgg cgagctccga ctccgcctcc | 660 |
| gccgccgcca ccggcaaggg cgtgctcctc aacttcgagg acggcgaggg gaaggtgtgg | 720 |
| cgattccggt actcgtactg gaacagcagc cagagctacg tgctgaccaa ggggtggagc | 780 |
| cgattcgtga gggagaaggg cctccgcgcc ggcgacacca tagtcttctc ccgctcggcg | 840 |
| tacggccccg acaagctgct cttcatcgac tgcaagaaga caacgcggc ggcggcgacc | 900 |
| accacctgcg ccggcgacga gaggccaacc acaagcggcg ccgaaccacg cgtcgtgagg | 960 |
| ctcttcggcg tcgacatcgc cggcggcgat tgccggaagc gggagagggc ggtggagatg | 1020 |
| gggcaagagg tcttcctact gaagaggcaa tgcgtggttc atcagcgtac tcctgcccta | 1080 |
| ggtgccctgc tgttatag | 1098 |

<210> SEQ ID NO 25
<211> LENGTH: 954
<212> TYPE: DNA
<213> ORGANISM: Oryza sativa

<400> SEQUENCE: 25

| | |
|---|---:|
| atggagcaag aagctgccat ggtcgtcttc tcctgcaact ccggctccgg tgggtcgtcg | 60 |
| tcgacgaccg attcaaagca agaggaggag gaggaggagg agttggccgc aatggaggaa | 120 |
| gacgagttga tccacgtcgt ccaggcggcg gagctgcggc tgccgtcgtc gacgacggcg | 180 |
| acgcggccgt cgtcgcggta caaggggtg gtgccgcagc cgaacgggcg gtgggggcg | 240 |
| cagatctacg agcggcacgc gcgggtgtgg ctcgggacgt tccccgacga ggaggcggcg | 300 |
| gcgcgcgcct acgacgtggc ggcgctccgc ttcggggc gcgacgccgt caccaaccgc | 360 |
| gccccggcgg cggagggcgc gtccgccggc gagctcgcgt tcctgccgc gcactccaag | 420 |
| gcggaggtcg tggacatgct gcggaagcac acctacgacg acgagctcca gcagggcctc | 480 |

```
cgccgcggct cgcgcgcgca gccgacgccg cggtgggcgc gcgagccgct gttcgagaag    540
gccgtgacgc cgagcgacgt cggcaagctc aaccgcctcg tggtgcccaa gcagcaggcc    600
gagaggcatt tcccgttccc gctccgccgc cacagctccg acgccgccgg caagggcgtg    660
ctcctcaact tcgaggacgg cgacggcaag gtgtggcgat ccggtactc gtactggaac     720 agcagccaga gttacgtgct caccaagggg tggagccgat tcgtgaggga aagggcctc     780 cgaccaggcg acaccgtggc cttctcccgg tcggcggcgg cgtgggggac ggagaagcac    840
ctcctcatcg actgcaagaa gatggagagg aacaacctgg caaccgtcga cgacgatgcc    900
cgtgtcgtcg tcaagctgtt cggcgttgac atcgccggag acaagacgag gtaa          954
```

```
<210> SEQ ID NO 26
<211> LENGTH: 936
<212> TYPE: DNA
<213> ORGANISM: Oryza sativa

<400> SEQUENCE: 26
```

```
atggagttca tcacgccaat cgtgaggccg gcatcggcgg cggcgggcgg cggcgaggtg     60
caggagagtg gtgggaggag cttggcggcg gtggagaagg agcacatgtt cgacaaggtg    120
gtgacgccga cgacgtggg gaagctgaac cggctggtga tcccgaagca gcacgcggag     180
aagtacttcc cgctggacgc ggcgtccaac gagaaggggc tcctgctcag cttcgaggac    240
cgcacgggga agccatggcg gttccgctac tcctactgga acagcagcca gagctacgtg    300
atgaccaagg ggtggagccg cttcgtcaag gagaagcgac tcgacgccgg ggacaccgtc    360
tccttcggcc gcgcgtcgg cgaggccgcg cgcggggagc tcttcatcga ctggcgccgc    420
cgccccgacg tcgtcgccgc gctccagccg cccacgcacc gcttcgccca ccacctccct    480
tcctccatcc ccttcgctcc ctgggcgcac accacggac acggagccgc cgccgccgcc    540
gccgccgccg ccggcgccag gtttctcctg cctccctcct cgactcccat ctacgaccac    600
caccgccgac acgccacgc cgtcgggtac gacgcgtacg ccgcggccac cagcaggcag    660
gtgctgttct accggccgtt gccgccgcag cagcagcatc atcccgcggt ggtgctggag    720
tcggtgccgg tgcgcatgac ggcggggcac gcggagccgc cgtcggctcc gtcgaagcga    780
gttcggctgt tcggggtgaa cctcgactgc gcgaattccg aacaagacca cgccggcgtg    840
gtcgggaaga cggcgccgcc gccgctgcca tcgccgccgt catcatcgtc atcttcctcc    900
gggaaagcga ggtgctcctt gaaccttgac ttgtga                              936
```

```
<210> SEQ ID NO 27
<211> LENGTH: 57
<212> TYPE: PRT
<213> ORGANISM: Nicotiana tabacum

<400> SEQUENCE: 27
```

```
Ser Arg Tyr Glu Gly Val Val Pro Gln Pro Asn Gly Arg Trp Gly Ala
1               5                   10                  15

Gln Ile Tyr Glu Lys His Gln Arg Val Trp Leu Gly Thr Phe Asn Glu
            20                  25                  30

Glu Asn Glu Ala Ala Arg Ala Tyr Asp Val Ala Ala Gln Arg Phe Arg
        35                  40                  45

Gly Arg Asp Ala Val Thr Asn Phe Lys
    50                  55
```

```
<210> SEQ ID NO 28
<211> LENGTH: 57
```

```
<212> TYPE: PRT
<213> ORGANISM: Capsicum sp.

<400> SEQUENCE: 28

Ser Lys Tyr Lys Gly Val Val Pro Gln Pro Asn Gly Arg Trp Gly Ala
 1               5                  10                  15

Gln Ile Tyr Glu Lys His Gln Arg Val Trp Leu Gly Thr Phe Asn Glu
             20                  25                  30

Glu Asn Glu Ala Ala Arg Ala Tyr Asp Val Ala Ala Gln Arg Phe Arg
         35                  40                  45

Gly Arg Asp Ala Val Thr Asn Phe Lys
     50                  55

<210> SEQ ID NO 29
<211> LENGTH: 58
<212> TYPE: PRT
<213> ORGANISM: Arabidopsis thaliana

<400> SEQUENCE: 29

Ser Arg Phe Lys Gly Val Val Pro Gln Pro Asn Gly Arg Trp Gly Ala
 1               5                  10                  15

Gln Ile Tyr Glu Lys His Gln Arg Val Trp Leu Gly Thr Phe Asn Glu
             20                  25                  30

Glu Asp Glu Ala Ala Arg Ala Tyr Asp Val Ala Ala His Arg Phe Arg
         35                  40                  45

Gly Arg Asp Ala Val Thr Asn Phe Lys Asp
     50                  55

<210> SEQ ID NO 30
<211> LENGTH: 57
<212> TYPE: PRT
<213> ORGANISM: Arabidopsis thaliana

<400> SEQUENCE: 30

Ser Lys Tyr Lys Gly Val Val Pro Gln Pro Asn Gly Arg Trp Gly Ala
 1               5                  10                  15

Gln Ile Tyr Glu Lys His Gln Arg Val Trp Leu Gly Thr Phe Asn Glu
             20                  25                  30

Glu Glu Glu Ala Ala Ser Ser Tyr Asp Ile Ala Val Arg Arg Phe Arg
         35                  40                  45

Gly Arg Asp Ala Val Thr Asn Phe Lys
     50                  55

<210> SEQ ID NO 31
<211> LENGTH: 58
<212> TYPE: PRT
<213> ORGANISM: Arabidopsis thaliana

<400> SEQUENCE: 31

Lys Tyr Lys Gly Val Val Gln Gln Asn Gly His Trp Gly Ala Gln
 1               5                  10                  15

Ile Tyr Ala Asp His Lys Arg Ile Trp Leu Gly Thr Phe Lys Ser Ala
             20                  25                  30

Asp Glu Ala Ala Thr Ala Tyr Asp Ser Ala Ser Ile Lys Leu Arg Ser
         35                  40                  45

Phe Asp Ala Asn Ser His Arg Asn Phe Pro
     50                  55

<210> SEQ ID NO 32
```

```
<211> LENGTH: 58
<212> TYPE: PRT
<213> ORGANISM: Arabidopsis thaliana

<400> SEQUENCE: 32

Thr Lys Phe Lys Gly Val Val Gln Gln Asn Gly His Trp Gly Ala
1               5                   10                  15

Gln Ile Tyr Ala Asp His Arg Arg Ile Trp Leu Gly Thr Phe Lys Ser
                20                  25                  30

Ala His Glu Ala Ala Ala Ala Tyr Asp Ser Ala Ser Ile Lys Leu Arg
            35                  40                  45

Ser Phe Asp Ala Asn Ser His Arg Asn Phe
        50                  55

<210> SEQ ID NO 33
<211> LENGTH: 58
<212> TYPE: PRT
<213> ORGANISM: Arabidopsis thaliana

<400> SEQUENCE: 33

Ser Lys Tyr Lys Gly Val Val Pro Gln Pro Asn Gly Arg Trp Gly Ala
1               5                   10                  15

Gln Ile Tyr Glu Lys His Gln Arg Val Trp Leu Gly Thr Phe Asn Glu
                20                  25                  30

Gln Glu Glu Ala Ala Arg Ser Tyr Asp Ile Ala Ala Cys Arg Phe Arg
            35                  40                  45

Gly Arg Asp Ala Val Val Asn Phe Lys Asn
        50                  55

<210> SEQ ID NO 34
<211> LENGTH: 58
<212> TYPE: PRT
<213> ORGANISM: Arabidopsis thaliana

<400> SEQUENCE: 34

Ser Lys Tyr Lys Gly Val Val Pro Gln Pro Asn Gly Arg Trp Gly Ala
1               5                   10                  15

Gln Ile Tyr Glu Lys His Gln Arg Val Trp Leu Gly Thr Phe Asn Glu
                20                  25                  30

Glu Asp Glu Ala Ala Arg Ala Tyr Asp Val Ala Val His Arg Phe Arg
            35                  40                  45

Arg Arg Asp Ala Val Thr Asn Phe Lys Asp
        50                  55

<210> SEQ ID NO 35
<211> LENGTH: 56
<212> TYPE: PRT
<213> ORGANISM: Oryza sativa

<400> SEQUENCE: 35

Ser Lys Phe Lys Gly Val Val Pro Gln Pro Asn Gly Arg Trp Gly Ala
1               5                   10                  15

Gln Ile Tyr Glu Arg His Gln Arg Val Trp Leu Gly Thr Phe Ala Gly
                20                  25                  30

Glu Asp Asp Ala Ala Arg Ala Tyr Asp Val Ala Ala Gln Arg Phe Arg
            35                  40                  45

Gly Arg Asp Ala Val Thr Asn Phe
        50                  55
```

```
<210> SEQ ID NO 36
<211> LENGTH: 56
<212> TYPE: PRT
<213> ORGANISM: Oryza sativa

<400> SEQUENCE: 36

Ser Lys Phe Lys Gly Val Val Pro Gln Pro Asn Gly Arg Trp Gly Ala
1               5                   10                  15

Gln Ile Tyr Glu Arg His Gln Arg Val Trp Leu Gly Thr Phe Ala Gly
            20                  25                  30

Glu Asp Asp Ala Ala Arg Ala Tyr Asp Val Ala Ala Gln Arg Phe Arg
        35                  40                  45

Gly Arg Asp Ala Val Thr Asn Phe
    50                  55

<210> SEQ ID NO 37
<211> LENGTH: 57
<212> TYPE: PRT
<213> ORGANISM: Oryza sativa

<400> SEQUENCE: 37

Ser Lys Tyr Lys Gly Val Val Pro Gln Pro Asn Gly Arg Trp Gly Ala
1               5                   10                  15

Gln Ile Tyr Glu Arg His Gln Arg Val Trp Leu Gly Thr Phe Thr Gly
            20                  25                  30

Glu Ala Glu Ala Ala Arg Ala Tyr Asp Val Ala Ala Gln Arg Phe Arg
        35                  40                  45

Gly Arg Asp Ala Val Thr Asn Phe Arg
    50                  55

<210> SEQ ID NO 38
<211> LENGTH: 56
<212> TYPE: PRT
<213> ORGANISM: Oryza sativa

<400> SEQUENCE: 38

Arg Tyr Lys Gly Val Val Pro Gln Pro Asn Gly Arg Trp Gly Ala Gln
1               5                   10                  15

Ile Tyr Glu Arg His Ala Arg Val Trp Leu Gly Thr Phe Pro Asp Glu
            20                  25                  30

Glu Ala Ala Ala Arg Ala Tyr Asp Val Ala Ala Leu Arg Tyr Arg Gly
        35                  40                  45

Arg Asp Ala Ala Thr Asn Phe Pro
    50                  55

<210> SEQ ID NO 39
<211> LENGTH: 53
<212> TYPE: PRT
<213> ORGANISM: Oryza sativa

<400> SEQUENCE: 39

Tyr Lys Gly Val Val Pro Gln Pro Asn Gly Arg Trp Gly Ala Gln Ile
1               5                   10                  15

Tyr Glu Arg His Ala Arg Val Trp Leu Gly Thr Phe Pro Asp Glu Glu
            20                  25                  30

Ala Ala Ala Arg Ala Tyr Asp Val Ala Ala Leu Arg Phe Arg Gly Arg
        35                  40                  45

Asp Ala Val Thr Asn
    50
```

-continued

<210> SEQ ID NO 40
<211> LENGTH: 60
<212> TYPE: PRT
<213> ORGANISM: Nicotiana tabacum

<400> SEQUENCE: 40

Leu Phe Glu Lys Ala Val Thr Pro Ser Asp Val Gly Lys Leu Asn Arg
1               5                   10                  15

Leu Val Ile Pro Lys Gln His Ala Glu Lys His Phe Pro Leu Gln Asn
            20                  25                  30

Gly Asn Thr Ser Lys Gly Val Leu Leu Asn Phe Glu Asp Leu Asn Gly
        35                  40                  45

Lys Val Trp Arg Phe Arg Tyr Ser Tyr Trp Asn Ser
    50                  55                  60

<210> SEQ ID NO 41
<211> LENGTH: 60
<212> TYPE: PRT
<213> ORGANISM: Capsicum sp.

<400> SEQUENCE: 41

Leu Phe Glu Lys Ala Val Thr Pro Ser Asp Val Gly Lys Leu Asn Arg
1               5                   10                  15

Leu Val Ile Pro Lys Gln His Ala Glu Lys His Phe Pro Leu Gln Asn
            20                  25                  30

Gly Asn Asn Ser Lys Gly Val Leu Leu Asn Phe Glu Asp Leu Asn Gly
        35                  40                  45

Lys Val Trp Arg Phe Arg Tyr Ser Tyr Trp Asn Ser
    50                  55                  60

<210> SEQ ID NO 42
<211> LENGTH: 60
<212> TYPE: PRT
<213> ORGANISM: Arabidopsis thaliana

<400> SEQUENCE: 42

Leu Phe Glu Lys Thr Val Thr Pro Ser Asp Val Gly Lys Leu Asn Arg
1               5                   10                  15

Leu Val Ile Pro Lys His Gln Ala Glu Lys His Phe Pro Leu Pro Leu
            20                  25                  30

Gly Asn Asn Asn Val Ser Val Lys Gly Met Leu Leu Asn Phe Glu Asp
        35                  40                  45

Val Asn Gly Lys Val Trp Arg Phe Arg Tyr Ser Tyr
    50                  55                  60

<210> SEQ ID NO 43
<211> LENGTH: 60
<212> TYPE: PRT
<213> ORGANISM: Arabidopsis thaliana

<400> SEQUENCE: 43

Leu Phe Glu Lys Thr Val Thr Pro Ser Asp Val Gly Lys Leu Asn Arg
1               5                   10                  15

Leu Val Ile Pro Lys Gln His Ala Glu Lys His Phe Pro Leu Pro Ala
            20                  25                  30

Met Thr Thr Ala Met Gly Met Asn Pro Ser Pro Thr Lys Gly Val Leu
        35                  40                  45

Ile Asn Leu Glu Asp Arg Thr Gly Lys Val Trp Arg
    50                  55                  60

<210> SEQ ID NO 44
<211> LENGTH: 60
<212> TYPE: PRT
<213> ORGANISM: Arabidopsis thaliana

<400> SEQUENCE: 44

Leu Phe Gln Lys Glu Leu Thr Pro Ser Asp Val Gly Lys Leu Asn Arg
1               5                   10                  15

Leu Val Ile Pro Lys Lys Tyr Ala Val Lys Tyr Met Pro Phe Ile Ser
                20                  25                  30

Ala Asp Gln Ser Glu Lys Glu Glu Gly Glu Ile Val Gly Ser Val Glu
            35                  40                  45

Asp Val Glu Val Val Phe Tyr Asp Arg Ala Met Arg
        50                  55                  60

<210> SEQ ID NO 45
<211> LENGTH: 60
<212> TYPE: PRT
<213> ORGANISM: Arabidopsis thaliana

<400> SEQUENCE: 45

Leu Phe Gln Lys Glu Leu Thr Pro Ser Asp Val Gly Lys Leu Asn Arg
1               5                   10                  15

Leu Val Ile Pro Lys Lys Tyr Ala Val Lys Tyr Met Pro Phe Ile Ser
                20                  25                  30

Asp Asp Gln Ser Glu Lys Glu Thr Ser Glu Gly Val Glu Asp Val Glu
            35                  40                  45

Val Val Phe Tyr Asp Arg Ala Met Arg Gln Trp Lys
        50                  55                  60

<210> SEQ ID NO 46
<211> LENGTH: 60
<212> TYPE: PRT
<213> ORGANISM: Arabidopsis thaliana

<400> SEQUENCE: 46

Leu Phe Glu Lys Ala Val Thr Pro Ser Asp Val Gly Lys Leu Asn Arg
1               5                   10                  15

Leu Val Ile Pro Lys Gln His Ala Glu Lys His Phe Pro Leu Pro Ser
                20                  25                  30

Pro Ser Pro Ala Val Thr Lys Gly Val Leu Ile Asn Phe Glu Asp Val
            35                  40                  45

Asn Gly Lys Val Trp Arg Phe Arg Tyr Ser Tyr Trp
        50                  55                  60

<210> SEQ ID NO 47
<211> LENGTH: 60
<212> TYPE: PRT
<213> ORGANISM: Arabidopsis thaliana

<400> SEQUENCE: 47

Leu Phe Glu Lys Ala Val Thr Pro Ser Asp Val Gly Lys Leu Asn Arg
1               5                   10                  15

Leu Val Ile Pro Lys His His Ala Glu Lys His Phe Pro Leu Pro Ser
                20                  25                  30

Ser Asn Val Ser Val Lys Gly Val Leu Leu Asn Phe Glu Asp Val Asn
            35                  40                  45

Gly Lys Val Trp Arg Phe Arg Tyr Ser Tyr Trp Asn

```
                50                  55                  60

<210> SEQ ID NO 48
<211> LENGTH: 60
<212> TYPE: PRT
<213> ORGANISM: Oryza sativa

<400> SEQUENCE: 48

Leu Phe Asp Lys Thr Val Thr Pro Ser Asp Val Gly Lys Leu Asn Arg
1               5                   10                  15

Leu Val Ile Pro Lys Gln His Ala Glu Lys His Phe Pro Leu Gln Leu
            20                  25                  30

Pro Ser Ala Gly Gly Glu Ser Lys Gly Val Leu Leu Asn Phe Glu Asp
        35                  40                  45

Ala Ala Gly Lys Val Trp Arg Phe Arg Tyr Ser Tyr
    50                  55                  60

<210> SEQ ID NO 49
<211> LENGTH: 60
<212> TYPE: PRT
<213> ORGANISM: Oryza sativa

<400> SEQUENCE: 49

Leu Phe Asp Lys Thr Val Thr Pro Ser Asp Val Gly Lys Leu Asn Arg
1               5                   10                  15

Leu Val Ile Pro Lys Gln His Ala Glu Lys His Phe Pro Leu Gln Leu
            20                  25                  30

Pro Ser Ala Gly Gly Glu Ser Lys Gly Val Leu Leu Asn Phe Glu Asp
        35                  40                  45

Ala Ala Gly Lys Val Trp Arg Phe Arg Tyr Ser Tyr
    50                  55                  60

<210> SEQ ID NO 50
<211> LENGTH: 60
<212> TYPE: PRT
<213> ORGANISM: Oryza sativa

<400> SEQUENCE: 50

Leu Phe Asp Lys Thr Val Thr Pro Ser Asp Val Gly Lys Leu Asn Arg
1               5                   10                  15

Leu Val Ile Pro Lys Gln His Ala Glu Lys His Phe Pro Leu Gln Leu
            20                  25                  30

Pro Pro Pro Thr Thr Thr Ser Ser Val Ala Ala Ala Asp Ala Ala
        35                  40                  45

Ala Gly Gly Gly Asp Cys Lys Gly Val Leu Leu Asn
    50                  55                  60

<210> SEQ ID NO 51
<211> LENGTH: 60
<212> TYPE: PRT
<213> ORGANISM: Oryza sativa

<400> SEQUENCE: 51

Leu Phe Glu Lys Ala Val Thr Pro Ser Asp Val Gly Lys Leu Asn Arg
1               5                   10                  15

Leu Val Val Pro Lys Gln His Ala Glu Lys His Phe Pro Leu Arg Arg
            20                  25                  30

Ala Ala Ser Ser Asp Ser Ala Ser Ala Ala Thr Gly Lys Gly Val
        35                  40                  45
```

```
Leu Leu Asn Phe Glu Asp Gly Glu Gly Lys Val Trp
    50                  55                  60

<210> SEQ ID NO 52
<211> LENGTH: 60
<212> TYPE: PRT
<213> ORGANISM: Oryza sativa

<400> SEQUENCE: 52

Leu Phe Glu Lys Ala Val Thr Pro Ser Asp Val Gly Lys Leu Asn Arg
1               5                   10                  15

Leu Val Val Pro Lys Gln Gln Ala Glu Arg His Phe Pro Phe Pro Leu
                20                  25                  30

Arg Arg His Ser Ser Asp Ala Ala Gly Lys Gly Val Leu Leu Asn Phe
            35                  40                  45

Glu Asp Gly Asp Gly Lys Val Trp Arg Phe Arg Tyr
    50                  55                  60
```

ENDOGENOUS REGULATOR OF RNA SILENCING IN PLANTS

CROSS REFERENCE TO RELATED APPLICATION

The present application is a divisional application of U.S. application Ser. No. 11/921,385 having a 35 U.S.C. 371 entry date of Apr. 13, 2009, which is the United States national entry of International Patent Application Number PCT/US05/19400 having a filing date of Jun. 2, 2005, which is incorporated herein in its entirety.

STATEMENT REGARDING FEDERALLY SPONSORED RESEARCH OR DEVELOPMENT

This invention was made with Government support under grant No. 5R01GM061014-04 awarded by the U.S. National Institutes of Health of the Department of Health and Human Services. The Government has certain rights in the invention.

SEQUENCE LISTING

The instant application contains a Sequence Listing which has been submitted electronically in ASCII format and is hereby incorporated by reference in its entirety. Said ASCII copy, created on May 22, 2014, is named USC-185-PCTUS-DIV_SL.txt and is 75,561 bytes in size.

BACKGROUND OF THE INVENTION (1) Field of the Invention

The present invention relates to methods of modulating gene expression in plants and to novel proteins and nucleotide sequences, and in particular, to methods of using such novel proteins and nucleotides for regulating the effects of post transcriptional gene silencing in plants.

(2) Description of the Related Art

With the advent of recombinant DNA technology in the 1970s, the genetic manipulation of plants entered a new age. Genes and traits previously unavailable through traditional breeding became available through DNA recombination, and with greater specificity than ever before. Commercially important genes from sexually incompatible plants, animals, bacteria or insects can now be successfully introduced into plants. Products of modern plant genetic engineering are already on the market, and examples include such transgenic plants as slow-softening tomatoes, cotton and corn plants resistant to herbicides and insects, and soybeans with altered fatty acid profiles. With many more products in the pipeline, the genetic engineering of plants is expected to have a profound impact on the future of agriculture.

Modern plant genetic engineering can involve the transfer of a desired gene into the plant genome and regeneration of a whole plant from the transformed tissue. Unfortunately, many of these efforts have been met with mixed results with regards to predictable and sustainable levels of gene expression.

Many factors affect gene expression in plants. One mechanism, RNA silencing, is an important regulatory mechanism that has only recently been intensively studied. RNA silencing is characterized by reduced levels of the specific mRNA encoded by the silenced gene. Individual cases of silencing include those in which mRNA level is regulated transcriptionally and those in which it is regulated post-transcriptionally.

RNA silencing in transgenic plants was first discovered after genetic transformation of plant tissues with multiple copies of an exogenous transgene that shared some homology with an endogenous gene. Researchers noticed that over time, high levels of exogenous gene expression would unexplainably falter and drop to low levels.

Recently, it has been reported that RNA silencing can be induced by plant virus infections in the absence of any known homology between the viral genome and an endogenous gene. It has been proposed that gene silencing may have evolved as a defense mechanism against viral invasion.

All genomes, including those of plants, animals, and fungi have specific defense mechanisms against infection by foreign bioactive agents. Thus, it has been proposed that RNA silencing is an ancestral mechanism that plant cells use as a defense against invading nucleotide molecules in a sequence specific manner. Therefore, one emerging view is that RNA silencing is part of a sophisticated network of interconnected pathways for cellular defenses (e.g., against viruses and transposons), RNA surveillance, and development, and that it could become a powerful tool to manipulate gene expression.

When viruses or transgenes are introduced into plants, they often trigger a particular host response that is generally referred to as post-transcriptional gene silencing (PTGS) or cosuppression. The mechanism of PTGS is believed to be similar to that of RNA interference (RNAi) in animals. The process appears to be initiated by double-stranded RNA (dsRNA) molecules, which may be generated by replicative intermediates of viral RNAs or by aberrant transgene-coded RNAs (these RNA molecules may become double-stranded when copied and/or amplified by an RNA-dependent RNA polymerase). The dsRNAs are digested into 21-23 nucleotide (nt) small interfering RNAs (siRNA). Evidence indicates that siRNAs are produced when the enzyme Dicer, a member of the RNase III family of dsRNA-specific ribonucleases, digests dsRNA in an ATP-dependent, processive manner. Successive cleavage events degrade the RNA to 19-21 bp duplexes (siRNAs), each with 2-nucleotide 3' overhangs. The conversion of dsRNA into siRNAs requires additional protein co-factors that may recruit the dsRNA to Dicer or stabilize the siRNA.

These siRNAs direct the degradation of target mRNAs complementary to the siRNA sequence by subsequently binding to a nuclease complex to form what is known as the RNA-induced silencing complex (RISC). Thereafter, the RISC complex binds and destroys the complementary target mRNAs, which in turn, leads to the silenced target RNA phenotype.

As mentioned previously, in both plants and animals, RNA silencing has evolved, at least in part, as an antiviral defense pathway. In response, many viruses have developed genes that encode suppressors of silencing. For example, it has been reported that certain plant viruses encode proteins that can suppress RNA silencing. One suppressor protein in particular, helper component-proteinase (HC-Pro), is produced by a number of plant potyviruses. HC-Pro acts to suppress transgene-induced silencing by interfering with the accumulation of the 21-23 nucleotide siRNAs. It has been found that infection of transgenic plants by viruses expressing HC-Pro can cause wholesale suppression of RNA silencing, resulting in the stabilization of target gene expression. For several reasons, however, it is not desirable to use the viral HC-Pro protein as a vector to suppress silencing. Furthermore, in cases where suppression of silencing is undesirable, actual resistance to HC-Pro suppression is required.

These recent studies on RNA silencing have furthered the understanding of the regulatory mechanisms underlying gene expression. However, In order to better utilize transgenic plants, the mechanisms behind transgene expression and endogenous gene suppression need to be controllable. The ability to quickly and easily create knock out phenotypes using protein components of the RNA silencing pathway would be desirable in terms of plant biotechnology.

From the foregoing, it can be seen that a need exists for improved methods of modulating gene expression in plant cells and plants, and in particular, for methods of regulating—by either reducing or enhancing—the expression of a certain target genes in plants. Such methods are needed to control gene suppression and to obtain acceptable expression levels of genes of interest.

SUMMARY

Briefly therefore, the present invention is directed to a novel method of regulating gene silencing in a plant cell, the method comprising modulating in the plant cell the amount of and/or the activity of a RAV protein.

The present invention is also directed to a novel method of regulating post transcriptional gene silencing in a plant, the method comprising: controlling in the plant the expression of a gene that encodes a RAV protein; or controlling in the plant the amount of and/or the activity of a RAV protein.

The present invention is also directed to a novel isolated nucleic acid molecule comprising the nucleotide sequence of SEQ ID NO:1, or a sequence that is substantially identical thereto.

The present invention is also directed to a novel chimeric gene comprising the nucleotide sequence of SEQ ID NO:1, or a sequence that is substantially identical thereto, operably linked to suitable regulatory sequences.

The present invention is also directed to a novel recombinant vector for transformation of plant cells, the vector comprising a polynucleotide having the sequence of SEQ ID NO:1, or a sequence that is substantially identical thereto.

The present invention is also directed to a novel plant cell comprising an introduced nucleotide sequence according to SEQ ID NO:1, or a sequence that is substantially identical thereto.

The present invention is also directed to a novel plant comprising an introduced nucleotide sequence according to SEQ ID NO:1, or a sequence that is substantially identical thereto.

The present invention is also directed to a novel plant seed comprising an introduced nucleotide sequence according to SEQ ID NO:1, or a sequence that is substantially identical thereto.

The present invention is also directed to a novel isolated protein comprising the amino acid sequence of SEQ ID NO:2, or a sequence that is substantially identical thereto.

The present invention is also directed to a novel antibody that binds with a protein comprising the amino acid sequence of SEQ ID NO:2, or a sequence that is substantially identical thereto, or binds with a polynucleotide comprising the nucleic acid sequence of SEQ ID NO:1, or a sequence that is substantially identical thereto.

Among the several advantages found to be achieved by the present invention, therefore, may be noted the provision of novel proteins and polynucleotides and to methods which use the novel proteins and polynucleotides to control RNA silencing of a target gene in a host cell and thereby to effectively modulate expression of the target gene.

BRIEF DESCRIPTION OF THE DRAWINGS

FIG. 5 shows a comparison of the percent amino acid similarity between ntRAV and several RAV proteins from *Arabidopsis thaliana*, and RAV-related proteins from pepper and rice;

FIGS. 6A and 6B shows a comparison of the amino acid sequences of ntRAV versus six RAV proteins from *Arabidopsis thaliana*; FIG. 6 discloses SEQ ID NOS: 6, 5, 7, 4, 3, 8 and 2, respectively, in order of appearance.

FIGS. 7A and 7B shows a comparison of the amino acid sequences of ntRAV versus five RAV-related proteins from rice; FIG. 7 discloses SEQ ID NOS: 13, 14, 10, 11, 12 and 2, respectively, in order of appearance.

FIG. 8 shows a comparison of the amino acid sequences of ntRAV (SEQ ID NO: 2) versus a RAV-related protein (SEQ ID NO: 9) from pepper;

FIG. 9 shows a GUS-silenced L-1 line of *Arabidopsis* sp. plant having wild-type RAV-2 gene on the left and on the right, a GUS-silenced L-1 line of *Arabidopsis* sp. plant having a knockout of its RAV-2 gene by a T-DNA insertion, and illustrating the enhancement of sense transgene silencing in the knockout plant by more extensive reduction in the expression of GUS as indicated by its lighter colored leaves; and FIGS. 10A and 10B shows a comparison of the amino acid sequences of the AP2 and B3 DNA binding sites of ntRAV with the amino acid sequences of comparable sites of other RAV proteins. FIG. 10 discloses SEQ ID NOS: 27-52, respectively, in order of appearance.

DETAILED DESCRIPTION OF THE PREFERRED EMBODIMENTS

Figure 1:
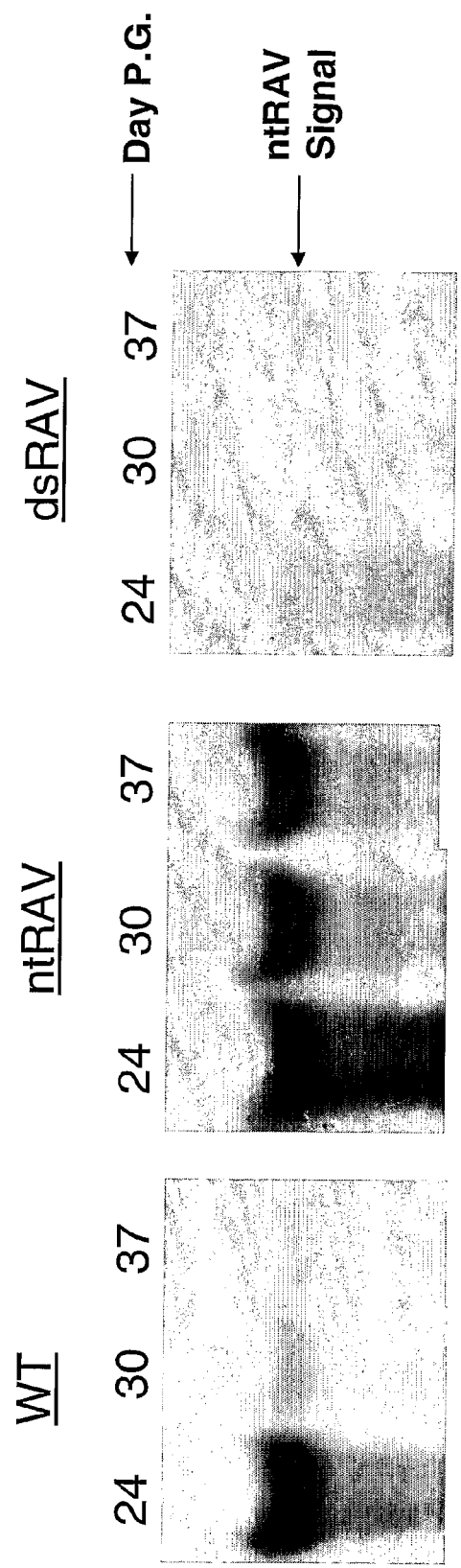
FIG. 1 shows photographs of Northern Blot panels that indicate the levels of ntRAV in samples taken from leaves of wild type tobacco plants (WT), from tobacco plants that overexpressed ntRAV with a 35S promoter (ntRAV), and from the knockdown line of tobacco plants having reduced levels of ntRAV expression (dsRAV), at 24, 30 and 37 days post germination (P.G.)

In accordance with the present invention, it has been discovered that RNA post transcriptional gene silencing in plants can be regulated by modulating in the plant cell the amount of and/or the activity of a member of the RAV family of proteins, which is described below in detail. One such RAV protein includes an amino acid sequence according to SEQ ID NO: 2, and has been shown to act an endogenous suppressor of post transcriptional gene silencing. The RAV protein having SEQ ID NO:2 is encoded for by a nucleotide sequence of SEQ ID NO:1. Because this protein was originally isolated from tobacco (*Nicotiniana tabacum*), and due to its similarity with proteins of the RAV family of *Arabidopsis thaliana*, the protein that includes the amino acid sequence of SEQ ID NO:2 is referred to herein as "ntRAV".

The term "modulating", as used herein in relation to affecting the amount of a protein in a plant cell, means taking action that increases the amount of the protein in the cell or taking action that decreases the amount of the protein in the cell. As used herein in relation to affecting the activity of a protein in a plant cell, the term "modulating" means taking action that increases the biological activity of the protein in the plant cell or taking action that decreases the biological activity of the protein in the cell. It is preferred that any action that is taken, within the meaning of the present invention, is one that permits the plant cell to continue to live and function.

In particular, it has been discovered that when a RAV protein is overexpressed in plants, it delays the onset of RNA silencing, thus allowing longer expression of a normally silenced target gene. Conversely, when the amount of or the expression of this same protein is decreased by various means, the target genes are silenced more rapidly and more effectively. Moreover, when the amount of or the expression of this protein is decreased, the plant can be made to be less susceptible to the RNA silencing-suppressing effects of plant viruses expressing proteins such as HC-Pro.

It has been shown that by modulating the amount of and/or the activity of ntRAV protein in a plant cell, one can regulate the RNA silencing mechanism of the cell. For example, by reducing the amount of ntRAV protein in the cell, the expression of deleterious genes can be turned off. Historically, such silencing has often been incomplete. Thus, knocking out the expression of ntRAV protein is a useful way to increase the effectiveness of RNA silencing in cases where such upregulation is desirable. Conversely, in some instances, RNA silencing limits biotechnologies aimed at high level gene expression in plants. Thus, overexpression of ntRAV protein is useful in delaying/suppressing silencing in situations where that is the desired outcome. In the latter case, the ntRAV protein might be useful in conjunction with other viral and endogenous suppressors of silencing, such as HC-Pro, or rgs-CaM, for example, to enhance or reduce their effectiveness. For additional information about the activity of rgs-CaM, see Anandalakshmi, R. et al., *Science,* 290.142-144 (2000).

When ntRAV is over-expressed in tobacco, the plants display a delay in the onset of RNA silencing induced by a sense transgene. When expression of the ntRAV protein is knocked down using an RNAi construct, the onset of sense transgene silencing is accelerated. Furthermore, more effective silencing occurs in adult plants when the expression of this protein is reduced. In addition, knockout of a related gene in *Arabidopsis thaliana* using a T-DNA insertion into the gene also enhances sense transgene silencing. These results suggest that the ntRAV protein that is described herein, and substantially identical proteins, are strong endogenous negative regulators (suppressors) of RNA silencing. Thus, genetic manipulation of the expression of the gene encoding this protein, and/or modulation of the level of the ntRAV protein itself, provides a mechanism to alter RNA silencing—either to suppress it or enhance it.

RNA silencing is frequently used to reduce the expression of deleterious genes in plants. However, many plant viruses encode proteins that suppress RNA silencing. Thus, infection by certain plant viruses potentially endangers the RNA silencing in engineered plants. In particular, the potyviruses encode a potent suppressor of RNA silencing that is capable of reversing silencing even when it has already been established in the plant. The RAV-related proteins that are the subject of this patent are, in part, defined by their interaction with HC-Pro and HC-Pro may well suppress RNA silencing via alterations in RAV activity. When the expression of RAV-related proteins is reduced or knocked out in either tobacco or *Arabidopsis*, RNA silencing is enhanced (i.e. it occurs faster and to a greater extent than in wildtype plants). The enhanced silencing is beneficial in cases where silencing is desired. In addition, it is possible that plants in which expression or activity of RAV-related proteins has been altered may be resistant to HC-Pro suppression of RNA silencing. Thus, if HC-Pro suppresses silencing via alterations in RAV-related activities, then it would not be able to suppress silencing in RAV knock-out plants. Because the potyviruses that encode HC-Pro are common, HC-Pro resistant RNA silencing would be very beneficial in cases where RNA silencing is desired.

In summary, it has been found that overexpression of ntRAV delays the onset of silencing in transgenic plants (e.g., tobacco). Knockdown of expression of the protein in tobacco enhances silencing, allowing silencing to occur more rapidly and more effectively. Knockout of a related transcription factor in *Arabidopsis* also enhances RNA silencing. There is no developmental phenotype associated with altered expression of the ntRAV protein. It is also believed that knockout of the gene encoding this protein may eliminate the ability of the viral suppressor of silencing termed HC-Pro to block RNA silencing.

The present invention includes, in one embodiment, a novel protein (i.e., ntRAV), which interacts with a plant viral suppressor of silencing called HC-Pro in a yeast two-hybrid system. As mentioned above, ntRAV comprises the amino acid sequence of SEQ ID NO.2, which is coded for by the polynucleotide sequence of SEQ ID NO.1. Related proteins, several of which are described below, have been identified that share the characteristic of utility for the regulation of gene silencing in plants, and they are included in the scope of an embodiment of the present invention.

ntRAV is a member of a group of related proteins. These proteins are distinguished by the presence of two distinct DNA binding motifs called AP2 and B3. This is a unique feature of the RAV and RAV-like proteins. See Kagaya, Y. et al., *Nucleic Acids Res.*, 27:470-478 (1999). Other DNA binding proteins commonly have one DNA binding motif or one or more copies of the same DNA binding motif. Only the RAVs have two distinct types of DNA binding motifs and this feature distinguishes them from all other proteins. Further description of the AP2 binding domain can be found in Jofuku, K. D. et al., *Plant Cell*, 6:1211-1225 (1994), and Ohme-Takagi, M. et al., *Plant Cell*, 7:173-182 (1995). Further information about the B3 binding domain can be found in Giraudat, J. et al., *Plant Cell*, 4:1251-1261 (1992), and McCarty, D. R. et al., *Cell*, 66:895-905 (1991). FIG. 18 shows a comparison of the AP2 and B3 DNA binding motif sequences of ntRAV with those from related proteins in pepper (csRAV), *Arabidopsis* (six proteins with At numbers) and rice (five proteins starting with "gi"). The percent similarity of each protein sequence with ntRAV is indicated after the name of the protein. The similarity data for the two DNA binding motifs along with the overall similarity of the whole protein to ntRAV is presented in the table shown in FIG. 5.

As used herein, ntRAV and all RAV and RAV-like proteins will be included in the terms "RAV protein". Likewise, genes that encode ntRAV and any RAV and RAV-like proteins will be included in the terms "RAV gene", or "gene encoding a RAV protein", or the like. A RAV protein, as defined herein, is a protein having both AP2 and B3 DNA binding domains. When it is said that a RAV protein has an AP2 DNA binding domain, it is meant that the protein contains an amino acid sequence that has at least a 50% similarity to the amino acid sequence between amino acids 63 and 119 of ntRAV. It is preferred that the RAV protein has an amino acid sequence that has at least a 60% similarity to the amino acid sequence between amino acids 63 and 119 of ntRAV, more preferred is a similarity of at least 70%, and yet more preferred is a similarity of at least 80%. The meaning of similarity between respective amino acid sequences and nucleic acid sequences is explained below.

The amino acid sequence of the AP2 binding domain of ntRAV is shown in SEQ ID NO:27, and includes amino acids 63-119. Comparable AP2 binding domains on other RAV proteins are shown in FIG. 10, and include AP2 binding domains for pepper (csRAV, SEQ ID NO:28), six RAV proteins from *Arabidopsis thaliana* (At proteins, SEQ ID NOS:29-34), and five rice RAV proteins (gi proteins, SEQ ID NOS:35-39). Percent similarity is shown for each sequence as compared to the AP2 binding site of ntRAV.

When it is said that a RAV protein has a B3 DNA binding domain, it is meant that the protein contains an amino acid sequence that has at least a 40% similarity to the amino acid sequence between amino acids 197 and 256 of ntRAV (with numbering starting from the amino end). It is preferred that the RAV protein has an amino acid sequence that has at least a 60% similarity to the amino acid sequence between amino acids 197 and 256 of ntRAV, more preferred is a similarity of at least 70%, and yet more preferred is a similarity of at least 80%.

The amino acid sequence of the B3 binding domain of ntRAV is shown in SEQ ID NO:40, and includes amino acids 197-256. Comparable B3 binding domains on other RAV proteins are shown in FIG. 10, and include B3 binding domains for pepper (csRAV, SEQ ID NO:41), six RAV proteins from *Arabidopsis thaliana* (At proteins, SEQ ID NOS:42-47), and five rice RAV proteins (gi proteins, SEQ ID NOS:48-52). Percent similarity is shown for each sequence as compared to the B3 binding site of ntRAV.

In some embodiments of the present invention, polynucleotides that comprise nucleotide sequences which encode for the respective AP2 and B3 DNA binding domains of the RAV proteins are to be included in the scope of the invention. Because the nucleotide sequences of the genes encoding ntRAV and RAV proteins are known, identification of a RAV protein having an amino acid sequence that is within a defined range of similarity to an ntRAV AP2 or B3 binding site would also be considered to identify the corresponding nucleic acid that encodes for that protein. Thus, the polynucleotide encoding the RAV protein would be within the same range of similarity as expressed for the protein when compared with the nucleotide sequence that encodes the reference ntRAV protein AP2 or B3 binding site. For example, identification of a RAV protein having an amino acid sequence with 80% similarity to the AP2 site of ntRAV and 70% similarity to the B3 site of ntRAV, would also identify the polynucleotide that encoded the RAV protein, which would have 80% nucleic acid similarity to the nucleotide sequence encoding for the AP2 site of ntRAV and 70% similarity to the nucleotide sequence encoding for the B3 site of ntRAV.

The amino acid (polypeptide) sequence of Tobacco (*Nicotiana tabacum*) ntRAV is shown in SEQ ID NO:2. The amino acid sequences of six RAV transcription factors of *Arabidopsis thaliana* are shown as SEQ ID NOS:3-8. The amino acid sequences of a pepper RAV transcription factor is shown in SEQ ID NO:9, and the amino acid sequences of five RAV proteins from rice are shown as SEQ ID NOS: 10-14. It is believed that all of the proteins that include the amino acid sequences shown in SEQ ID NOS:2-14 are members of the RAV family of proteins.

A comparison of the amino acid sequence similarity of ntRAV with several RAV transcription factors of *Arabidopsis*, and with RAV-related proteins of pepper and rice is shown in FIG. 5. It can be seen that amino acid percent sequence identity ranges from 48.6% to 86.8%.

FIG. 6 shows a comparison of the amino acid sequence of ntRAV with several *Arabidopsis* RAV transcription factors. The same type of comparison is shown in FIG. 7 for rice RAV-related proteins, and in FIG. 8 for pepper RAV-related proteins.

The polynucleotide sequence that encodes ntRAV of tobacco is shown as SEQ ID NO:1. In addition, SEQ ID NOS: 15-26 show polynucleotide sequences that encode RAV proteins of *Arabidopsis*, pepper, and rice, respectively.

While not wishing to be bound by this or any other particular theory, it is believed that the ntRAV/HC-Pro interaction is indicative of ntRAV having a direct role in the HC-Pro suppression of silencing. For example, to determine if ntRAV plays a role in RNA silencing, wild type plants and plants overexpressing ntRAV were crossed to a tobacco transgenic line containing a silenced GUS sense-transgene, and the progeny were analyzed for the expression of the ntRAV and GUS genes. The endogenous ntRAV gene is expressed at high levels in seedlings and then decreases precipitously at about 3 weeks, the same time that silencing of the GUS sense-transgene initiates. The expression of high levels of ntRAV is extended by about 2 weeks in the ntRAV overexpressing line, and the onset of RNA silencing is delayed correspondingly. A high level of ntRAV is therefore correlated with inability of plants to initiate silencing of GUS sense-transgenes. This result raises the possibility that the RAV proteins directly or indirectly control expression or activity of components of the silencing mechanism.

The invention overcomes the limitations of the prior art by providing methods and compositions for modulating silencing of gene expression in plants, and thereby modulating gene expression itself. In particular, the present invention encompasses a novel protein (i.e., ntRAV, and proteins that are substantially identical) and a novel method of using a family of proteins (i.e., RAV proteins) that are related to the *Arabidopsis thaliana* RAV family, and which are capable of modulating RNA silencing of particular coding sequences, even when provided in the absence of viral factors.

The present invention is useful for modulating the expression of one or more target genes by modulating RNA silencing. The present invention can accomplish such modulation by overexpressing or knockout of one or more of the endogenous RAV sequences described herein. For example, overexpression of one or more of the RAV sequences leads to suppressed RNA silencing and therefore, enhanced target gene expression. Conversely, reduced expression of one or more of the endogenous RAV sequences leads to enhanced RNA silencing and therefore, suppressed target gene expression.

Therefore, in one embodiment, the present invention may find particular use for enhancing expression of one or more transgenes by suppressing RNA silencing through overexpression of one or more of the RAV proteins described herein, as silencing of transgenes can frequently occur, especially when transgenes are present in more than one copy in a genome. This affect may be achieved without the need for fusions between a transgene coding sequence and one of the RAV sequences described herein, or alternatively, using such a fusion.

In another embodiment, the present invention may find particular use for suppressing the expression of one or more transgenes by enhancing RNA silencing through the reduction of expression of one or more of the endogenous RAV proteins described herein. Likewise, this affect may be achieved without the need for fusions between a transgene coding sequence and one of the RAV proteins described herein, or alternatively, using such a fusion.

Compositions and methods for modulating the expression of a target sequence in a plant are provided. That is, the expression of the target sequence may be enhanced or decreased. In preferred embodiments, a reduced expression of the target sequence is effected.

The target sequence comprises any sequence of interest, including genes, regulatory sequences, and the like. Genes of interest include those encoding agronomic traits, insect resistance, disease resistance, herbicide resistance, sterility, grain characteristics, and the like. The genes may be involved in metabolism of oil, starch, carbohydrates, nutrients, and the like. Genes or traits of interest include, but are not limited to, environmental- or stress-related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, and the like.

The invention relates to the modulation of RNA silencing of a target gene, and in preferred embodiments, the enhancement of RNA silencing of a target gene in plants. The terms "RNA silencing of a target gene" are generally used to refer to suppression of expression of a gene. The degree of reduction may be partial or total reduction in production of the encoded gene product. Therefore, these terms should not be taken to require complete "silencing" of expression of a gene.

The methods and compositions of the invention are useful in any situation where modulation of the expression of a nucleotide sequence in a plant cell is desired. Thus, the methods are useful for modulating the expression of endogenous as well as exogenous sequences. For example, for exogenous sequences, the endogenous RAV sequences described herein can be overproduced or RAV can be added in order to enhance expression of genes normally silenced by transgene-induced gene silencing. In other examples, expression of one or more of the RAV sequences may be blocked or reduced, or the activity or amount of the RAV protein can by inhibited or reduced in order to more effectively suppress expression of a target gene that is normally silenced. Therefore, the target sequence may be any nucleotide sequence of interest.

Overexpression of RAV in a plant cell can be accomplished by operably linking one or more of the RAV sequences described herein to any exogenous promoter that would allow for stronger expression that the RAV endogenous promoter. For example, operably linking a RAV sequence to a cauliflower mosaic virus 35S promoter in a suitable expression cassette and then inserting such an expression cassette into a plant cell could give overexpression of ntRAV transcripts and/or RAV polypeptides.

Suppression of endogenous RAV expression and commensurate reduction of a target gene's expression can be accomplished by creating a "knock-out" or "disruption" of one or more of the endogenous RAV sequences identified herein and then allowing homologous recombination between the endogenous RAV gene and the disrupted knock-out nucleic acid sequence. A knock-out or disrupted RAV sequence can be prepared by inserting a "non-RAV" sequence within the endogenous RAV sequence or by rearranging or deleting parts of the RAV sequence and then inserting the disrupted RAV sequence into a host cell. Suitable non-RAV sequences that could knock-out the endogenous RAV expression could be selectable markers or any other such markers.

As used herein, the term "DNA" means deoxyribonucleic acid. As used herein, the term "cDNA" means complementary deoxyribonucleic acid.

As used herein, the terms "coding sequence" mean a polynucleotide sequence that is translated in an organism to produce a protein. The term "coding DNA sequence" is a DNA sequence from which the information for making a peptide molecule, mRNA or tRNA are transcribed. A DNA sequence may be a gene, combination of genes, or a gene fragment.

As used herein, "complementary" polynucleotides are polynucleotides that are capable of base-pairing according to the standard Watson-Crick complementarity rules. Specifically, purines will base pair with pyrimidines to form combinations of guanine paired with cytosine (G:C) and adenine paired with either thymine (A:T) in the case of DNA, or adenine paired with uracil (A:U) in the case of RNA. Two polynucleotides may hybridize to each other if they are complementary to each other, or if each has at least one region that is substantially complementary to the other.

As used herein, the term "gene" should be understood to refer to a unit of heredity. Each gene is composed of a linear chain of deoxyribonucleotides which can be referred to by the sequence of nucleotides forming the chain. Thus, "sequence" is used to indicate both the ordered listing of the nucleotides which form the chain, and the chain itself, which has that sequence of nucleotides. The term "sequence" is used in the similar way in referring to RNA chains, linear chains made of ribonucleotides. The gene may include regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different strains of the same type of organism, or even within a particular strain of the organism, without altering the identity of the gene.

As used herein, the term "heterologous" is used to indicate a recombinant DNA sequence in which the DNA sequence and the associated DNA sequence are isolated from organisms of different species or genera.

A polynucleotide may be "introduced" or "transformed" into any cell by any means known to those of skill in the art, including transfection, transformation or transduction, transposable elements, electroporation, *Agrobacterium* infection, polyethylene glycol-mediated uptake, particle bombardment, and the like. The introduced polynucleotide may be maintained in the cell stably if it is incorporated into a non-chromosomal autonomous replicon or integrated into the genome of the host cell. Alternatively, the introduced polynucleotide may be present on an extra-chromosomal non-replicating vector and be transiently expressed or transiently active. As used herein, the term "transform" or "introduce" refers to the introduction of a polynucleotide (single or double stranded DNA, RNA, or a combination thereof) into a living cell by any means. Transformed cells, tissues and plants encompass not only the end product of a transformation process, but also the progeny thereof, which retain the polynucleotide of interest.

As used herein, the term "isolated polynucleotide" is a polynucleotide that is substantially free of the nucleic acid sequences that normally flank the polynucleotide in its naturally occurring replicon. For example, a cloned polynucleotide is considered isolated. Alternatively, a polynucleotide is considered isolated if it has been altered by human intervention, or placed in a locus or location that is not its natural site, or if it is introduced into a cell by agroinfection.

As used herein, a "normal" or "endogenous" form of a gene (wild type) is a form commonly found in natural populations of an organism. Commonly a single form of a gene will predominate in natural populations. In general, such a gene is suitable as a normal form of a gene; however, other forms which provide similar functional characteristics may also be used as a normal gene. In particular, a normal form of a gene does not confer a growth conditional phenotype on the organism having that gene, while a mutant form of a gene suitable for use in these methods can provide such a growth conditional phenotype.

As used herein, "nucleic acid" and "polynucleotide" refer to RNA or DNA that is linear or branched, single or double stranded, or a hybrid thereof. The polynucleotides of the invention may be produced by any means, including genomic preparations, cDNA preparations, in vitro synthesis, RT-PCR and in vitro or in vivo transcription. The term "polynucleotide" means a chain of at least two nucleotides joined together. The chain may be linear, branched, circular or combinations thereof. Nucleotides are generally those molecules selected for base-pairing and include such molecules as guanine, cytosine, adenine, uracil, and thymine.

As used herein, the term "operatively linked to" or "associated with" means two DNA sequences which are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

As used herein, the term "plant" refers to whole plants, plant organs and tissues (e.g., stems, roots, ovules, fruit, stamens, leaves, embryos, meristematic regions, callus tissue, gametophytes, sporophytes, pollen, microspores and the like), seeds, plant cells and the progeny thereof.

As used herein, the term "plant tissue" is any tissue of a plant in its native state or in culture. This term includes, without limitation, whole plants, plant cells, plant organs, plant seeds, protoplasts, callus, cell cultures, and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "plant transformation vector" is a plasmid or viral vector that is capable of transforming plant tissue such that the plant tissue contains and expresses DNA that was not pre-existing in the plant tissue.

As used herein, the term "polypeptide" means a chain of at least two amino acids joined by peptide bonds. The chain may be linear, branched, circular or combinations thereof. Preferably, polypeptides are from about 10 to about 1000 amino acids in length, more preferably 10-50 amino acids in length. The polypeptides may contain amino acid analogs and other modifications, including, but not limited to glycosylated or phosphorylated residues.

As used herein, the term "recombinant polynucleotide" refers to a polynucleotide that has been altered, rearranged or modified by genetic engineering. Examples include any cloned polynucleotide, and polynucleotides that are linked or joined to heterologous sequences. Two polynucleotide sequences are heterologous if they are not naturally found joined together. The term recombinant does not refer to alterations to polynucleotides that result from naturally occurring events, such as spontaneous mutations.

As used herein, the term "RNA" means ribonucleic acid and the term "mRNA" means messenger RNA.

As used herein, the term "transgenic" refers to any cell, tissue, organ or organism that contains all or part of at least one recombinant polynucleotide. In many cases, all or part of the recombinant polynucleotide is stably integrated into a chromosome or stable extra-chromosomal element, so that it is passed on to successive generations.

Use of the term "transgenic" also refers to foreign polynucleotides. Use of the term "foreign" in this context refers to polynucleotides that may or may not have been altered, rearranged or modified or even that have also preexisted within the cell, tissue, organ or organism. As illustration, a foreign polynucleotide is any polynucleotide that is introduced or re-introduced into a cell, tissue, organ or organism regardless of whether the same or a similar polynucleotide has already preexisted there. Any addition of any polynucleotide to a cell, tissue, organ or organism is considered by the present invention to be encompassed by the term "transgenic."

As used herein, the term "transgenic plant" refers to any plant, plant cell, callus, plant tissue or plant part that contains all or part of at least one recombinant polynucleotide. In many cases, all or part of the recombinant polynucleotide is stably integrated into a chromosome or stable extra-chromosomal element, so that it is passed on to successive generations.

As used herein, the term "transgenic plant material" is any plant matter, including, but not limited to cells, protoplasts, tissues, leaves, seeds, stems, fruits and tubers both natural and processed, containing a recombinant polynucleotide. Further, plant material includes processed derivatives thereof including, but not limited to food products, food stuffs, food supplements, extracts, concentrates, pills, lozenges, chewable compositions, powders, formulas, syrups, candies, wafers, capsules and tablets.

The terms "reduced expression", "suppressed expression" or "knock out", which are used interchangeably herein, are intended to mean that the expression of a target sequence is suppressed over the expression of that sequence that is observed in conventional transgenic lines for heterologous sequences or over endogenous levels of expression for homologous sequences. Heterologous or exogenous sequences comprise sequences that do not occur in the plant of interest in its native state. Homologous or endogenous sequences are those that are natively present in the plant genome. Generally, expression of the target sequence is reduced at least about 10%, preferably about 30%, more preferably about 50%, and even more preferably about 80% and a greater degree of reduction of expression is yet more preferable. The methods of the invention provide for a substantial reduction in expression. However, it is not required that the reduction in expression have an effect on the plant that is observable by visual inspection.

Sequence relationships between two or more nucleic acids or polynucleotides are generally defined as sequence identity, percentage of sequence identity, and substantial identity. In determining sequence identity, a "reference sequence" is used as a basis for sequence comparison. The reference sequence may be a subset or the entirety of a specified sequence. That is, the reference sequence may be a full-length gene sequence or a segment of the gene sequence.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or two polypeptides, refers to two or more sequences or subsequences that have at least about 50% nucleotide or amino acid residue identity when compared and aligned for maximum correspondence as measured using one of the following sequence comparison algorithms or by visual inspection. In preferred embodiments, substantially identical sequences have at least about 60%, more preferably at least about 70%, yet more preferably at least about 80%, and even more preferably have about 90% or 95% nucleotide or amino acid residue identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical when they are identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48.443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al., *J. Mol. Biol.* 215: 403-410 (1990), and Altschul et al., *Nucleic Acids Res.* 25: 3389-3402 (1977), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As discussed above, sequence identity, or identity, in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Nucleotide sequences are generally substantially identical if the two molecules hybridize to each other under stringent conditions. Generally, stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This can occur when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. It is recognized that the temperature salt and wash conditions may be altered to increase or decrease stringency conditions. For the post-hybridization washes, the critical factors are the ionic strength and temperature of the final wash solution. See, Meinkoth and Wahl, *Anal. Biochem.* 138:267-284 (1984).

As indicated, fragments and variants of the peptide and nucleotide sequences of the invention are encompassed herein. By "fragment" is intended a portion of the sequence. In the case of a nucleotide sequence, fragments of the enhancer sequence will generally retain the biological activity of the native suppressor protein. Alternatively, fragments of the targeting sequence may or may not retain biological activity. Such targeting sequences may be useful as hybridization probes, as antisense constructs, or as co-suppression sequences. Thus, fragments of a nucleotide sequence may range from at least about 20 nucleotides, about 50 nucleotides, about 100 nucleotides, and up to the full-length nucleotide sequence of the invention.

The term "variants" means substantially similar sequences. For nucleotide sequences, conservative variants include those sequences that, because of the degeneracy of the genetic code, encode the amino acid sequence of the enhancer of the invention. Variant nucleotide sequences include synthetically derived sequences, such as those generated, for example, using site-directed mutagenesis. Generally, nucleotide sequence variants of the invention will have at least 40%, 50%, 60%, 70%, generally 80%, preferably 85%, 90%, up to 95%, 98% sequence identity to its respective native nucleotide sequence.

Variant suppressor or enhancer proteins may also be utilized. A "variant" protein is intended to include a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular CloningA Laboratory Manual*, Cold Spring Harbor Laboratory, Cold Spring Harbor, N.Y., (1989) or *Current Protocols in Molecular Biology* Volumes 1-3, John Wiley & Sons, Inc. (1994-1998).

One embodiment of the present invention includes a recombinant vector, which includes at least one isolated nucleic acid molecule of the present invention inserted into any vector capable of delivering the nucleic acid molecule into a cell. Such a vector contains heterologous nucleic acid sequences, that is, nucleic acid sequences that are not naturally found adjacent to nucleic acid molecules of the present invention and that preferably are derived from a species other than the species from which the nucleic acid molecule(s) are derived. The vector can be either RNA or DNA, and can be either prokaryotic or eukaryotic.

One type of recombinant vector, referred to herein as a recombinant molecule, comprises a nucleic acid molecule of the present invention operatively linked to control sequences within an expression vector. The phrase "operatively linked" refers to insertion of a nucleic acid molecule into an expression vector in a manner such that the molecule is able to be expressed when transformed into a cell. As used herein, an expression vector is a DNA or RNA vector that is capable of transforming a cell and of effecting expression of a specified nucleic acid molecule. Preferably, the expression vector is also capable of replicating within the cell. Expression vectors of the present invention include any vectors that function (i.e., direct gene expression) in recombinant cells of the present invention, including in bacterial, fungal, yeast, crustacean, mammalian, insect, other animal, and plant cells.

In preferred embodiments, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

Where appropriate, the RAV gene(s) for modulating RNA silencing may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831, and 5,436,391, and Murray et al., *Nucleic Acids Res.* 17:477-498 (1989).

Preferred expression vectors of the present invention can direct ntRAV overexpression or suppression in plant cells.

The present invention also provides vectors containing the expression cassettes of the invention. By "vector", what is meant is a polynucleotide sequence that is able to replicate in a host cell, but such definition also includes transient vectors that could be used to introduce DNA by, for example, homologous recombination in the genome, which do not replicate in a host cell. The vector can comprise DNA or RNA and can be single or double stranded, and linear or circular. Various plant expression vectors and reporter genes are described in Gruber et al. in *Methods in Plant Molecular Biology and Biotechnology*, Glick et al., eds, CRC Press, pp. 89-119 (1993); and Rogers et al., *Meth Enzymol* 153:253-277 (1987). Standard techniques for the construction of the vectors of the present invention are well-known to those of ordinary skill in the art and can be found in such references as Sambrook et al., Ibid.

The following vectors, which are commercially available, are provided by way of example. Among vectors preferred for use in bacteria are pQE70, pQE60 and pQE-9, available from Qiagen; pBS, pD10, phagescript, psiX174, pbluescript SK, pbsks, pNH8A, pNH16a, pNH18A, pNH46A, available from Stratagene; and ptrc99a, pKK223-3, pKK233-3, pDR540, pRIT5 available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in any host cell or tissue may be used in this aspect of the invention.

The vectors of the invention can contain 5' and 3' regulatory sequences necessary for transcription and termination of the polynucleotide of interest. Thus, the vectors can include a promoter and a transcriptional terminator.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., *PNAS USA* 86:6126-6130 (1989)); potyvirus leaders, for example, TEV leader (Tobacco Etch Virus) (Allison et al., MDMV leader (*Maize Dwarf Mosaic Virus*); *Virology* 154:9-20 (1986)), and human immunoglobulin heavy-chain binding protein (BiP), (Macejak et al., *Nature,* 353:90-94 (1991)); untranslated leader from the coat protein mRNA of alfalfa mosaic virus (AMV RNA 4) (Jobling et al., *Nature* 325:622-625 (1987)); tobacco mosaic virus leader (TMV) (Gallie et al. in Molecular Biology of RNA, ed. Cech (Liss, N.Y.), pp. 237-256 (1989)): and maize chlorotic mottle virus leader (MCMV) (Lommel et al., *Virology* 81:382-385 (1991)). See also, Della-Cioppa et al., *Plant Physiol.* 84:965-968 (1987).

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Other functional sequences may be included in the vectors of the inventions. Such functional sequences include, but are not limited to, introns, enhancers and translational initiation and termination sites and polyadenylation sites. Preferably, the expression cassettes of the present invention are engineered to contain a constitutive promoter 5' to its translation initiation codon (ATG) and a poly(A) addition signal (AATAAA) 3' to its translation termination codon. The control sequences can be those that can function in at least one plant, plant cell, plant tissue, or plant organ. These sequences may be derived from one or more genes, or can be created using recombinant technology.

Other elements such as introns, enhancers, polyadenylation sequences and the like may also be a part of the recombinant DNA. Such elements may or may not be necessary for the function of the DNA, but may provide improved expression of the mRNA by affecting transcription, stability, or the like. For example, the maize AdhlS first intron may be placed between the promoter and the coding sequence in a particular recombinant DNA construction. This intron, when included in a DNA construction, is known to increase production of a protein in maize cells. (J. Callis et al., *Genes and Develop.*, 1:1183 (1987)). However, sufficient expression for a selectable marker to perform satisfactorily can often be obtained without an intron. See T. Klein et al., *Plant Physiol.*, 91:440 (1989). An example of an alternative suitable intron is the shrunken-I first intron of *Zea mays*.

The 5' regulatory sequences (promoters) which are often used in creation of chimeric genes for plant transformation may cause either nominally constitutive expression in all cells of the transgenic plant, or regulated gene expression where only specific cells, tissues, or organs show expression of the introduced genes.

As used herein, the terms "promoter" or "regulatory DNA sequence" means an untranslated DNA sequence which assists in, enhances, or otherwise affects the transcription, translation or expression of an associated structural DNA sequence which codes for a protein or other DNA product. The promoter DNA sequence is usually located at the 5' end of a translated DNA sequence, typically between 20 and 100 nucleotides from the 5' end of the translation start site.

Promoters useful in the expression cassettes of the invention include any promoter that is capable of initiating transcription in a cell. Promoters which are known or found to cause transcription of a foreign gene in plant cells can be used in the present invention. Such promoters may be obtained from plants, bacteria, animals or viruses and include, but are not necessarily limited to the constitutive 35S promoter of cauliflower mosaic virus (CaMV) (as used herein, the phrase "CaMV 35S" promoter, includes variations of CaMV 35S promoter such as the 2×CaMV 35S promoter). See Odell et al., *Nature* 313:810-812 (1985). Constitutive promoters such as the 35S promoter are active under most conditions.

Examples of constitutive promoters that are useful in the present invention include the Sep1 promoter, the rice actin promoter (McElroy et al., *Plant Cell* 2:163-171 (1990)), the *Arabidopsis* actin promoter, the ubiquitan promoter (Christensen et al., *Plant Molec Biol* 18:675-689 (1989)); the pEmu promoter (Last et al., *Theor Appl Genet* 81:581-588 (1991)), the figwort mosaic virus 35S promoter, the Smas promoter (Velten et al., *EMBO J* 3:2723-2730 (1984)), the GRP1-8 promoter, the cinnamyl alcohol dehydrogenase promoter (U.S. Pat. No. 5,683,439), promoters from the T-DNA of *Agrobacterium*, such as those from the mannopine synthase, nopaline synthase, and octopine synthase genes, the small subunit of ribulose bisphosphate carboxylase (ssuRUBISCO) promoter, and the like. Other constitutive promoters include those in U.S. Pat. Nos. 5,608,149; 5,608,144; 5,604,121; 5,569,597; 5,466,785; 5,399,680; 5,268,463; and 5,608,142.

Developmental stage-preferred promoters are preferentially expressed at certain stages of development. Tissue and organ preferred promoters include those that are preferentially expressed in certain tissues or organs, such as fruits, leaves, roots, stems, seeds, or xylem. Examples of tissue preferred and organ preferred promoters include, but are not limited to Prha (expressed in root, seedling, lateral root, shoot apex, cotyledon, petiole, inflorescence stem, flower, stigma, anthers, and silique, and auxin-inducible in roots); VSP2 (expressed in flower buds, flowers, and leaves, and wound inducible); SUC2 (expressed in vascular tissue of cotyledons, leaves and hypocotyl phloem, flower buds, sepals and ovaries); AAP2 (silique-preferred); SUC1 (anther and pistil preferred); AAP1 (seed preferred); Saur-AC1 (auxin inducible in cotyledons, hypocotyl and flower); Enod 40 (expressed in root, stipule, cotyledon, hypocotyl and flower); and VSP1 (expressed in young siliques, flowers and leaves).

The present invention may utilize promoters for genes which are known to give high-level expression in edible plant parts, such as the tuber-specific patatin gene promoter from potato. For further information, see, e.g., H. C. Wenzler, et al, *Plant Mol. Biol.*, 12:41-50 (1989). It is also known that a tissue-specific promoter for one species may be used successfully in directing transgenic DNA expression in specific tissues of other species. For example, the potato tuber promoters will also function in tomato plants to cause fruit specific expression of an introduced gene. See U.S. patent Ser. No. 08/344,639, to Barry, et al.

A further example of a tissue-specific promoter is the seed specific bean phaseolin and soybean beta-conglycinin promoters. See, e.g., Keeler et al., *Plant. Mol. Biol.* 34:15-29 (1997).

Examples of other promoters for use with an embodiment of the present invention include fruit-specific promoters such as the E8 promoter, described in Deikman et al., *EMBO J.* 2:3315-3320 (1998). The activity of the E8 promoter is not limited to tomato fruit, but is thought to be compatible with any system wherein ethylene activates biological process, including fruit ripening. See U.S. Pat. No. 5,234,834 to Fischer et al. Other promoters suitable for use with the present invention are the MADS-box promoters, endo-β-1, 4-glucanase promoter, expansin promoters, egase promoters, pectate lyase promoter, polygalacturonase promoters, and ethylene biosynthesis promoters.

Also useful in the present invention are: (a) another tomato fruit-specific promoter, LeExp-1 (See U.S. Pat. No. 6,340,748); (b) the banana fruit-specific promoters known as the MT clones (See U.S. Pat. No. 6,284,946); and (c) several strawberry specific promoters termed GSRE2, GSRE49, SEL1, and SEL2 (See U.S. Pat. No. 6,080,914).

Leaf-specific promoters include, Yamamoto et al., *Plant J.* 12(2):255-265 (1997); Kwon et al., *Plant Physiol.* 105:357-67 (1994); Yamamoto et al., *Plant Cell Physiol.* 35(5):773-778 (1994); Gotor et al., *Plant J.* 3:509-18 (1993); Orozco et al., *Plant Mol. Biol.* 23(6):1129-1138 (1993); and Matsuoka et al., *Proc. Natl. Acad. Sci. USA* 90(20):9586-9590 (1993).

Root-specific promoters are known and can be selected from the many available from the literature. See, for example, Hire et al., *Plant Mol. Biol.* 20(2): 207-218 (1992) (soybean root-specific glutamine synthetase gene); Keller and Baumgartner, *Plant Cell* 3(10):1051-1061 (1991) (root-specific control element in the GRP 1.8 gene of French bean); Sanger et al., *Plant Mol. Biol.* 14(3):433-443 (1990) (root-specific promoter of the mannopine synthase (MAS) gene of *Agrobacterium tumefaciens*); Miao et al., *Plant Cell* 3(1):11-22 (1991) (full-length cDNA clone encoding cytosolic glutamine synthetase (GS), which is expressed in roots and root nodules of soybean). Bogusz et al., *Plant Cell* 2(7):633-641 (1990) (root-specific promoters from hemoglobin genes from the nitrogen-fixing nonlegume *Parasponia andcersonii* and the related non-nitrogen-fixing nonlegume *Trema tomentosa*). Leach and Aoyagi, *Plant Science (Limerick)* 79(1):69-76 (1991) (rolC and rolD root-inducing genes of *Agrobacterium rhizogenes*); Teer et al., *EMBO J.* 8(2):343-350 (1989) (octopine synthase and TR2' gene); (VfENOD-GRP3 gene promoter); Kuster et al., *Plant Mol.*

*Biol.* 29(4):759-772 (1995) and Capana et al., *Plant Mol. Biol.* 25(4):681-691 (1994) rolB promoter. See also U.S. Pat. Nos. 5,837,876; 5,750,386; 5,633,363; 5,459,252; 5,401,836; 5,110,732; and 5,023,179.

Anther or pollen-specific promoters may be used to create male sterile plants. While either the targeting sequence or the enhancer may be operably linked to such promoters, it may be preferred to express both the enhancer and the targeting sequence with an anther specific or pollen specific promoter to prevent even low expression of the toxin in other tissues of the plant.

"Seed-preferred" promoters include both "seed-specific" promoters (those promoters active during seed development such as promoters of seed storage proteins) as well as "seed-germinating" promoters (those promoters active during seed germination). See Thompson et al., *BioEssays* 10:108 (1989). Such seed-preferred promoters include, but are not limited to, Cim1 (cytokinin-induced message); cZ19B1 (maize 19 kDa zein); celA (cellulose synthase); gama-zein; Glob-1; bean .beta.-phaseolin; napin; .beta.-conglycinin: soybean lectin: cruciferin; maize 15 kDa zein; 22 kDa zein; 27 kDa zein; g-zein; waxy; shrunken 1; shrunken 2; globulin 1, etc.

A number of inducible promoters are known in the art, which can be used in conjunction with the present invention. For resistance genes, a pathogen-inducible promoter can be utilized. Such promoters include those from pathogenesis-related proteins (PR proteins), which are induced following infection by a pathogen, e.g., PR proteins, SAR proteins, beta-1,3-glucanase, chitinase, and the like. See, for example, Redolfi et al., *Neth. J Plant Pathol.* 89:245-254 (1983); Uknes et al., *Plant Cell* 4:645-656 (1992); and Van Loon, *Plant Mol. Virol.* 4:111-116 (1985). Of particular interest are promoters that are expressed locally at or near the site of pathogen injection. See, for example, Marineau et al., *Plant Mol. Biol.* 9:335-342 (1987); Matton et al., *Molecular Plant-Microbe Interactions* 2:325-331 (1989); Somsisch et al., *Proc. Natl. Acad. Sci. USA* 83:2427-2430 (1986): Somsisch et al., *Mol. Gen. Genet.*, 2:93-98 (1988); and Yang, *Proc. Natl. Acad. Sci. USA* 93:14972-14977 (1996). See also, Chen et al., *Plant J.* 10.955-966 (1996); Zhang et al., *Proc. Natl. Acad. Sci. USA* 91:2507-2511 (1994); Warner et al., *Plant J.*, 3:191-201 (1993): Siebertz et al., *Plant Cell* 1:961-968 (1989); U.S. Pat. No. 5,750,386; and Cordero et al., *Physiol. Mol. Plant Path.* 41:189-200 (1992).

Additionally, as pathogens find entry into plants through wounds or insect damage, a wound-inducible promoter may be used in the DNA constructs of the invention. Such wound-inducible promoters include potato proteinase inhibitor (pin II) gene (Ryan, Ann. *Rev. Phytopath.* 28:425-449 (1990); Duan et al., *Nature Biotechnology* 14:494-498 (1996); wun1 and wun2, U.S. Pat. No. 5,428,148; win1 and win2 (Stanford et al., *Mol. Gen. Genet.* 215:200-208 (1989)); systemin (McGurl et al., *Science* 225:1570-1573 (1992)); WIP1 (Rohmeier et al., *Plant Mol. Biol.* 22:783-792 (1993); Eckelkamp et al., *FEBS Letters* 323:73-76 (1993); MPI gene (Corderok et al., *Plant J.* 6(2):141-150 (1994)); and the like.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al., *Proc. Natl. Acad. Sci. USA* 88:10421-10425 (1991), and McNellis et al., *Plant J.* 14(2):247-257 (1998), and tetracycline-inducible and tetracycline-repressible promoters (see, for example, Gatz et al., *Mol. Gen. Genet.* 227:229-237 (1991), and U.S. Pat. Nos. 5,814,618 and 5,789,156).

The recombinant polynucleotides that are to be introduced into the plant cells will preferably contain either a selectable marker or a reporter gene, or both, in order to facilitate identification and selection of transformed cells. Alternatively, the selectable marker can be carried on a separate piece of DNA and used in a co-transformation procedure. Both selectable markers and reporter genes can be flanked with appropriate regulatory sequences to enable expression in plants. Useful selectable markers are well known in the art and include, for example, antibiotic and herbicide resistance genes. Examples of such markers include genes encoding drug or herbicide resistance, such as hygromycin resistance (hygromycin phosphotransferase (HPT)), spectinomycin resistance (encoded by the aada gene), kanamycin and gentamycin resistance (neomycin phosphotransferase (nptII)), streptomycin resistance (streptomycin phosphotransferase gene (SPT)), phosphinothricin or basta resistance (barnase (bar)), chlorsulfuron reistance (acetolactase synthase (ALS)), chloramphenicol resistance (chloramphenicol acetyl transferase (CAT)), G418 resistance, lincomycin resistance, methotrexate resistance, glyphosate resistance, and the like.

The expression cassettes of the invention may be covalently linked to genes encoding enzymes that are easily assayed, for example, luciferase, alkaline phosphatase, B-galactosidase (B-gal), B-glucuronidase (GUS), and the like.

Transcriptional termination regions include, but are not limited to, the terminators of the octopine synthase and nopaline synthase genes in the *A. tumefaciens* Ti plasmid. For further information, see Ballas et al., *Nuc Acid Res* 17:7891-7903 (1989). If translation of the transcript is desired, translational start and stop codons can also be provided.

Plants suitable for transformation according to the processes of this invention include, without limitation, both dicotyledon and monocotyledon plant cells can be used as a host organism in the present invention. For example, the present invention may be used for transformation of any plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia

*integrifolia*), almond (*Prunus amygdalus*), sugar beets (*Beta vulgaris*), oats, barley, vegetables, ornamentals, and conifers.

Preferably, plants of the present invention are crop plants (for example, cereals and pulses, maize, wheat, potatoes, tapioca, rice, *sorghum*, millet, cassava, barley, pea, and other root, tuber, or seed crops. Important seed crops are oil-seed rape, sugar beet, maize, sunflower, soybean, and *sorghum*. Horticultural plants to which the present invention may be applied may include lettuce, endive, and vegetable brassicas including cabbage, broccoli, and cauliflower, and carnations and geraniums. The present invention may be applied to tobacco, cucurbits, carrot, strawberry, sunflower, tomato, pepper, *chrysanthemum*, poplar, *eucalyptus*, and pine.

Grain plants that provide seeds of interest include oil-seed plants and leguminous plants. Seeds of interest include grain seeds, such as corn, wheat, barley, rice, *sorghum*, rye, etc. Oil seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Plants transformed with a DNA construct of the invention may be produced by standard techniques known in the art for the genetic manipulation of plants. The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

For example, various methods have been successfully demonstrated to transform plants in a stable manner. Such methods include, among others; *Agrobacterium*-mediated transformation, viral-mediated transformation, biolistics (microprojectile bombardment), protoplasts (PEG), electroporation, and microinjection. A typical procedure involves the mechanical, bacterial, or viral introduction of the foreign DNA, which encodes for the biosynthetic pathway or protein of interest, into immature plant parts. As the "transformed" immature plant develops, the foreign DNA becomes incorporated into the plant's own DNA.

Methods and compositions for transforming a bacterium, a fungal cell, a plant cell, or an entire plant with one or more expression vectors comprising an ntRAV protein-encoding gene segment are further aspects of this disclosure. A transgenic bacterium, fungal cell (such as, for example, a yeast cell), plant cell or plant derived from such a transformation process or the progeny and seeds from such a transgenic plant are also further embodiments of the invention. A variety of techniques are available for the introduction of the genetic material into or transformation of the plant cell host. However, the particular manner of introduction of the plant vector into the host is not critical to the practice of the present invention, and any method which provides for efficient transformation can be employed.

Methods for the introduction of polynucleotides into plants and for generating transgenic plants are known to those skilled in the art. See e.g. Weissbach & Weissbach, *Methods for Plant Molecular Biology*, Academic Press, N.Y.; Grierson & Corey (1988).

The choice of plant tissue source or cultured plant cells for transformation will depend on the nature of the host plant and the transformation protocol. Useful tissue sources include callus, suspension culture cells, protoplasts, leaf segments, root segments, stem segments, tassels, pollen, embryos, hypocotyls, tuber segments, meristematic regions, and the like. In preferred embodiments, the tissue source is regenerable, in that it will retain the ability to regenerate whole, fertile plants following transformation.

In a preferred embodiment of the present invention, the *Agrobacterium*-Ti plasmid system is utilized. *Agrobacterium tumefaciens*-meditated transformation techniques are well described in the scientific literature. See, e.g., Horsch et al, *Science* 233: 496-498 (1984). Descriptions of the *Agrobacterium* vector systems and methods for *Agrobacterium*-mediated gene transfer are provided in Gruber et al., supra. Although *Agrobacterium* is useful primarily in dicots, certain monocots can also be transformed by *Agrobacterium*. For instance, *Agrobacterium* transformation of maize is described in U.S. Pat. No. 5,550,318.

*Agrobacterium*-mediated transformation utilizes *A. tumefaciens*, the etiologic agent of crown gall, a disease of a wide range of dicotyledons and gymnosperms that results in the formation of tumors or galls in plant tissue at the site of infection. *Agrobacterium*, which normally infects the plant at wound sites, carries a large extrachromosomal element called Ti (tumor-inducing) plasmid.

Ti plasmids contain two regions required for tumor induction. One region is the T-DNA (transfer-DNA), which is the DNA sequence that is ultimately found stably transferred to plant genomic DNA. The other region is the vir (virulence) region, which has been implicated in the transfer mechanism. Although the vir region is absolutely required for stable transformation, the vir DNA is not actually transferred to the infected plant Transformation of plant cells mediated by infection with *A. tumefaciens* and subsequent transfer of the T-DNA alone have been well documented. See, e.g., Bevan, M. W. et al., *Int. Rev. Genet,* 16: 357 (1982).

The construction of an *Agrobacterium* transformation vector system has two elements. First, a plasmid vector is constructed which replicates in *Escherichia coli* (*E. coli*). This plasmid contains the DNA encoding the protein of interest (in this invention an over-expressed or knocked-out ntRAV transgene). This DNA is flanked by T-DNA border sequences that define the points at which the DNA integrates into the plant genome. Border sequences include both a left border (LB) and a right border (RB).

Usually a gene encoding a selectable marker (such as a gene encoding resistance to an antibiotic or herbicide such as hygromycin or Basta) is also inserted between the left border and right border sequences. The expression of this gene in transformed plant cells gives a positive selection method to identify those plants or plant cells which have an integrated T-DNA region. The second element of the process is to transfer the plasmid from *E. coli* to *Agrobacterium*. This can be accomplished via a conjugation mating system, or by direct uptake of plasmid DNA by *Agrobacterium* using such methods as electroporation.

Those skilled in the art would recognize that there are multiple choices of *Agrobacterium* strains and plasmid construction strategies that can be used to optimize genetic transformation of plants. They will also recognize that *A. tumefaciens* may not be the only *Agrobacterium* strain used. Other *Agrobacterium* strains such as *A. rhizogenes* might be more suitable in some applications. See Lichtenstein and Fuller in: *Genetic Engineering*, Volume 6, Ribgy (ed) Academic Press, London (1987).

Microprojectile bombardment, electroporation and direct DNA uptake are preferred where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

The present invention is not limited to the *Agrobacterium*-Ti plasmid system, and includes any direct physical method of introducing foreign DNA into an organism such as plant cells. Direct transformation involves the uptake of exogenous genetic material into cells or protoplasts. Such uptake may be enhanced by use of chemical agents or electric fields. See Dewulf J. and Negrutiu I., *Direct gene transfer into protoplasts: The chemical approach*, in: *A Laboratory Guide for Cellular and Molecular Plant Biology*. Eds. I. Negrutiu and G. Gharti-Chhetri. Birkhauser Verlag. Basel (1991). The exogenous genetic material may then be integrated into the nuclear genome. For mammalian cells, transfection procedures can be used. For bacterial cells, electroporation or heat shock methods can be employed.

For plant systems, direct gene transfer can also be accomplished by polyethylene glycol (PEG) mediated transformation. This method relies on chemicals to mediate the DNA uptake by protoplasts and is based on synergistic interactions between $Mg^{+2}$, PEG, and possibly $Ca^{+2}$. See, e.g., Negrutiu, R. et al., *Plant Mol. Biol.*, 8: 363 (1987). Alternatively, exogenous DNA can be introduced into cells or protoplasts by microinjection. In this technique, a solution of the plasmid DNA or DNA fragment is injected directly into the cell with a finely pulled glass needle.

Another procedure for direct gene transfer involves bombardment of cells by micro-projectiles carrying DNA. In this procedure, commonly called particle bombardment or biolistics, tungsten or gold particles coated with the exogenous DNA are accelerated toward the target cells. The particles penetrate the cells carrying with them the coated DNA. Microparticle acceleration has been successfully demonstrated to give both transient expression and stable expression in cells suspended in cultures, protoplasts, immature embryos of plants, including, but not limited to, onion, maize, soybean, and tobacco. Microprojectile transformation techniques are described in Klein T. M., et al, *Nature*, 327: 70-73 (1987).

Electric fields may also be used to introduce genetic material into the cells of an organism. The application of brief, high-voltage electric pulses to a variety of bacterial, animal and plant cells leads to the formation of nanometer-sized pores in the plasma membrane. DNA is taken directly into the cell cytoplasm either through these pores or as a consequence of the redistribution of membrane components that accompanies closure of the pores. Electroporation techniques are described in Fromm et al., *Proc. Natl. Acad. Sci.* 82: 5824 (1985).

Viral means of introducing DNA into cells are known in the art. In particular, a number of viral vector systems are known for the introduction of foreign or native genes into mammalian cells. These include the SV40 virus (See, e.g., Okayama et al, *Molec. Cell Biol.* 5:1136-1142 (1985)); bovine papilloma virus (See, e.g., DiMaio et al., *Proc. Natl. Acad. Sci. USA* 79:4030-4034 (1982)); adenovirus (See, e.g., Morin et al., *Proc. Natl. Acad. Sci. USA* 84:4626 (1987)). For further information regarding viral vector systems, see, e.g., Yifan et al., *Proc. Natl. Acad. Sci. USA* 92:1401-1405 (1995).

A number of viral vector systems are also known for the introduction of foreign or native genes into plant cells. A variety of plant viruses that can be employed as vectors are known in the art and include cauliflower mosaic virus (CaMV), geminivirus, brome mosaic virus, and tobacco mosaic virus.

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al., in *Cell Culture and Somatic Cell Genetics of Plants*, Vols. I, II, and III, *Laboratory Procedures and Their Applications* (Academic Press) (1984); and Weissbach et al., *Methods For Plant Mol. Biol.* (1989). The particular method of regeneration will depend on the starting plant tissue and the particular plant species to be regenerated. Plant regeneration from cultured protoplasts is described in Evans et al., Protoplasts Isolation and Culture, *Handbook of Plant Cell Culture*, Macmillilan Publishing Company, New York, pp. 124-176 (1983).

In recent years, it has become possible to regenerate many species of plants from callus tissue derived from plant explants. Regeneration of plants from tissue transformed with *A. tumefaciens* has been demonstrated for several species of plants. These include, but are not limited to, sunflower, tomato, white clover, rapeseed, cotton, tobacco, potato, maize, rice, and numerous vegetable crops.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Likewise, conventional plant breeding methods can be used, including, but not limited to crossing and backcrossing, self-pollination and vegetative propagation. Techniques for breeding plants are known to those skilled in the art.

The progeny of a transgenic plant are included within the scope of the invention, provided that the progeny contain all or part of the ntRAV transgenic construct. Thus, according to the invention there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed.

In addition to a plant, the present invention provides any clone of such a plant, seed, selfed or hybrid progeny and descendants, and any part of any of these, such as cuttings, seed. The invention provides any plant propagule that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant. Plant extracts and derivatives are also provided.

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples. In the examples, all percentages are given on a weight basis unless otherwise indicated.

Example 1

This example shows the production of both an ntRAV over-expressed tobacco line and an ntRAV-silenced transgenic tobacco line.

Transgenic tobacco lines were produced that over-expressed ntRAV and were silenced for ntRAV. Each of these lines were then crossed to a transgenic tobacco line ("6b5") that is silenced in response to a sense-transgene encoding beta-glucosidase (GUS). For example, transgenic tobacco plants overexpressing ntRAV were generated by introducing a transgene into tobacco cells that expressed ntRAV cDNA under control of the 35S cauliflower mosaic virus promoter. Transgenic plants partially silenced for ntRAV were generated by introducing a transgene that contained the ntRAV sequences in an inverted repeat (dsRAV) to induce the RNA silencing. Both the overexpressing and the knockdown transgenic tobacco lines were phenotypically wild-type.

The 6b5 Tobacco line was generated by cloning the bacterial UidA gene between the 35S promoter with a double enhancer and the terminator sequences of the pea rbcS 9C gene and introduced into tobacco plants by agroinfiltration. Tobacco line X-27-8 is *N. tabacum* cv *Xanthi* NC transformed with the wild-type PI/HC-Pro sequence. Line X-27-8 was constructed for the experiments reported here by transformation with *Agrobacterium*. Tobacco line ntRAV-OX was generated by cloning the full length ntRAV gene behind the 35s promoter of the pFGC-1008 plasmid and transformed into tobacco with *Agrobacterium*. The double stranded knock down construct was the same as the OX construct except that the initial full-length ntRA V sequence was followed by another ntRA V in reverse orientation and separated by a portion of the UidA gene.

Example 2

This example shows histochemical staining of the ntRAV over-expressed and silenced transgenic tobacco line.

Leaves were assayed for GUS activity as described but with minor modifications. For staining of GUS in tobacco leaf tissue the leaves were partially abraded on the lower side by using carborundum, fixed for 20 min in 90% acetone, vacuum infiltrated with a buffer containing 50 mM sodium phosphate (pH 7.2), 0.5 mM $K_3Fe(CN)_6$, 0.5 mM $K_3Fe(CN)_6$, and 1 mM 5-bromo-4-chloro-3-indolyl β-D-glucuronide and incubated at 37 deg C. Leaf pieces were subsequently treated with 95% ethanol to remove chlorophyll.

Example 3

This Example shows RNA Northern Analysis of the ntRAV over-expressed and silenced transgenic tobacco line.

Step 1: RNA Isolation

RNA isolation was carried out as follows. Tissues were frozen in liquid nitrogen and cells were disrupted in a mortar and pestle without allowing the tissue to thaw. Cells were then homogenized in buffer (0.1M LiCl, 0.1M Tris-HCl, 0.01M ethylene diamine tetra acetic acid and 1% sodium dodecyl sulfate) and phenol/chloroform extracted. The high molecular weight RNA is precipitated in 2M LiCl, spun down, washed in 75% EtOH, resuspended in $H_2O$ and quantified. The low molecular weight RNA is EtOH precipitated, resuspended in a smaller volume (200 ul) and separated from residual high molecular weight RNA and DNA in 10% polyethylene glycol. Enriched low molecular weight RNA is then EtOH precipitated and resuspended for quantification.

Step 2: Northern Blotting

Equal volumes (10 ul/lane) of high molecular weight RNA were fractionated in a 1% agarose gel using formaldehyde (0.66%) gel electrophoresis and blotted to Hybond N paper (Amersham Corp.) using capillary action as described by Maniatis (1982). But with the following modification. RNA samples were incubated in sample buffer containing 60% formamide at 85 deg. C. for 2 minutes and at 65 deg. C. for 10 minutes to insure denaturation of double stranded RNA. Equal volumes (15 µg/lane) of low molecular weight RNA were fractionated with denaturing polyacrylamide gel electrophoresis and blotted to Hybond N paper. Randomly labeled (+) strand RNA probes for mRNA hybridization and (−) strand RNA probes for siRNA hybridization were generated from PCR fragment templates via a transcription reaction using P32 alpha-labeled UTP.

Levels of ntRAV were measured by Northern Blot of samples taken from leaves of wild type tobacco plants (WT), from tobacco plants that overexpressed ntRAV with a 35S promoter (ntRAV), and from the knockdown line of tobacco plants having reduced levels of ntRAV expression (dsRAV), at 24, 30 and 37 days post germination (P.G.). All plants were cultivated under the same conditions. FIG. 1 shows that initiation of GUS silencing in the wild type 6b5 line (WT) occurred developmentally—the transgene was expressed in young seedlings, but declined with the onset of silencing at around three weeks after germination. In contrast, levels of ntRAV in the transgenic plants overexpressing ntRAV (ntRAV) show high levels of ntRAV at all three sampling times, whereas the knockdown line of plants (dsRAV) show low levels of ntRAV at all sampling times.

The ectopic over-expression of ntRAV delays the developmental onset of GUS silencing in leaves of the 6b5 line by about two weeks. However, once begun, the pattern of RNA silencing is similar in ntRAV over-expressing lines and wild-type controls, beginning in veins of older leaves and spreading into adjacent blade tissue.

Figure 2:
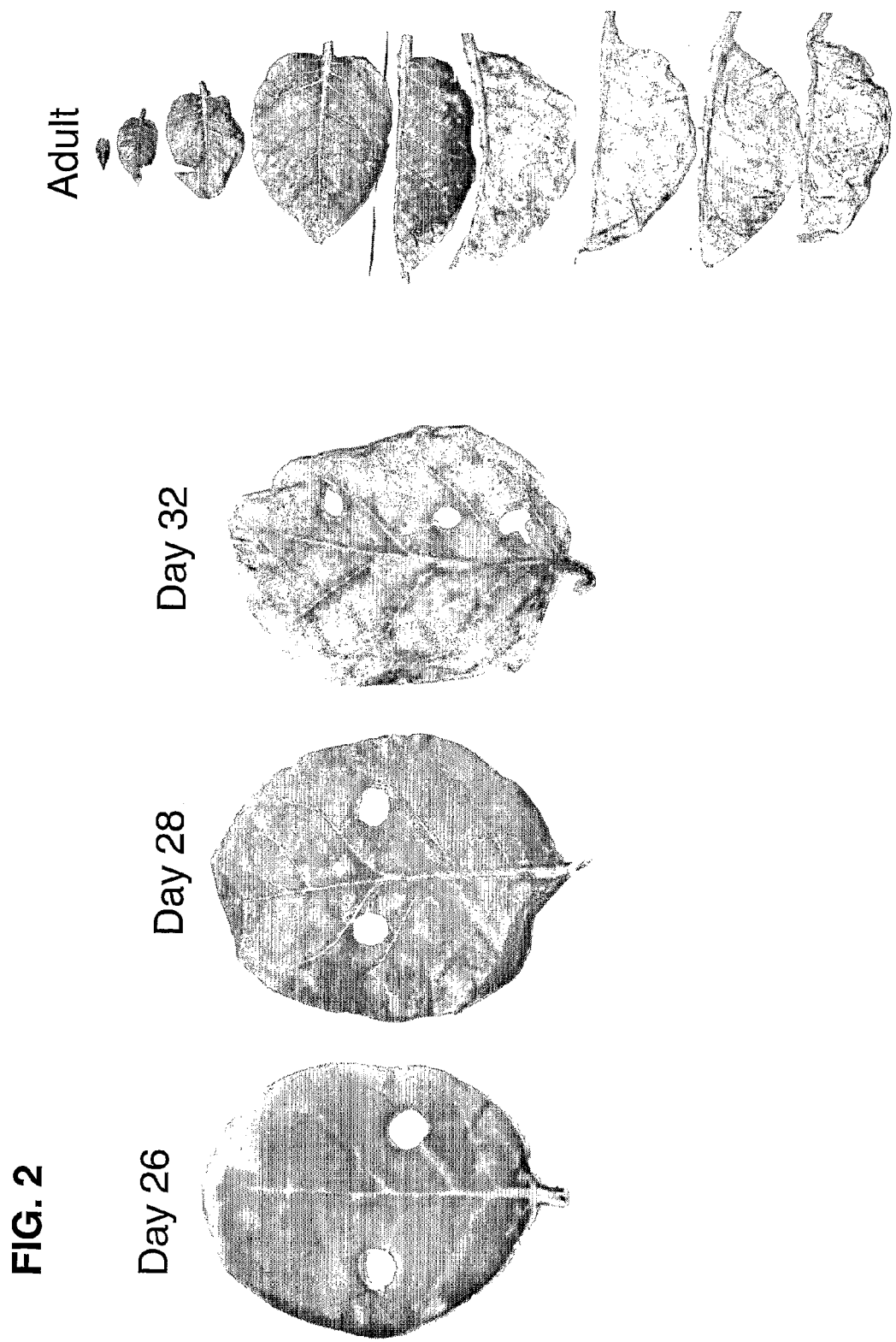
FIG. 2 illustrates the developmental silencing of a sense transgene encoding the reporter enzyme GUS in the tobacco transgenic line 6b5, wherein silencing is seen to occur developmentally through days 26, 28 and 32 P.G. and is seen to begin in the vascular system and spreads throughout the leaf; and also shown on the right is the progression of silencing in an adult plant from the bottom of the plant towards the top.

FIG. 2 illustrates the effects of sense transgene silencing of GUS in the wild type tobacco line (WT), wherein silencing is seen to occur developmentally. Silencing resets each generation. Silencing initiates during development, begins in the vascular system, and spreads throughout the leaf.

The pattern of accumulation of endogenous ntRAV mRNA parallels that of the silenced GUS mRNA, high in young seedlings and rapidly declining at two to three weeks after germination. Together, these data suggest that ntRAV encodes an endogenous suppressor of RNA silencing that acts early in development to block RNA silencing. Consistent with these data, it is believed that the onset of GUS silencing was accelerated in an ntRAV silenced tobacco line.

Figure 3:
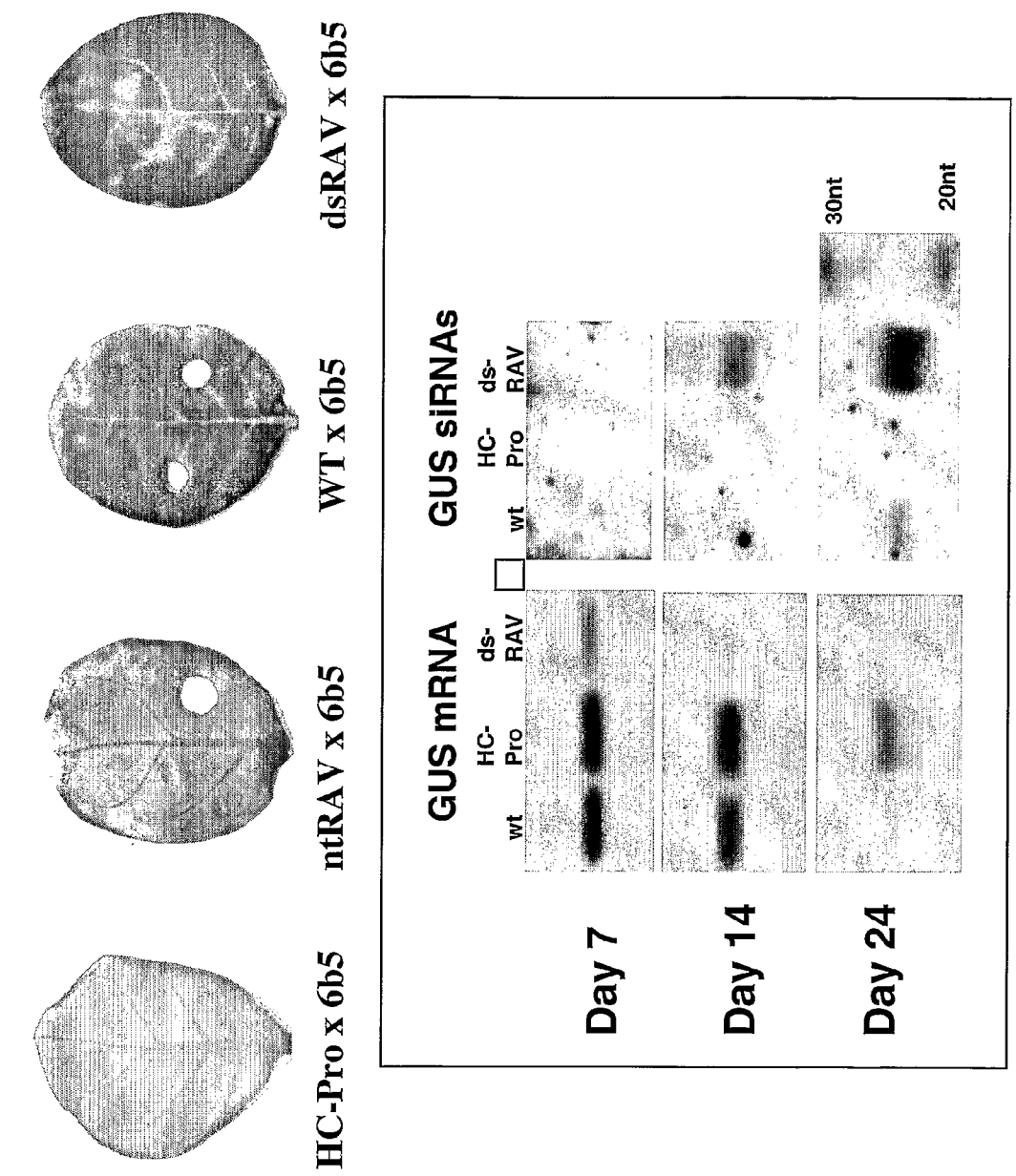
FIG. 3 shows the effect of reducing ntRAV expression on sense transgene silencing of the reporter gene GUS in tobacco transgenic line 6b5. Histochemical staining to localize GUS expression in plants at 24 days after germination is shown in the upper part of the figure. Shown at the far left is a leaf from the 6b5 transgenic plant that also expresses HC-Pro, a viral suppressor of RNA silencing (HC-Pro X 6b5). This leaf is dark colored throughout because silencing of the GUS gene is blocked. The second leaf from the left shows a leaf from a 6b5 transgenic plant that also over-expresses the ntRAV gene and is also suppressed for RNA silencing (ntRAV X 6b5). The third leaf from the left is from the 6b5 line in an otherwise wildtype background (WT X 6b5). This leaf shows the initiation of GUS silencing in the veins of the leaf: thus, the veins of the plants are not dark colored in some places due to lack of GUS activity. The last leaf on the right is from the 6b5 line that also carries a transgene that expresses double-stranded (ds) RNA for the endogenous ntRAV gene (dsRAV X 6b5). This leaf shows more extensive silencing of the GUS transgene as indicated by more extensive loss of color in the veins. Molecular data from the same plants is shown in the lower part of the figure. The level of GUS mRNA and GUS siRNAs is shown in the sense-transgene silenced 6b5 transgenic line at 7, 14 or 24 days post-germination in an otherwise wildtype background (wt) or in the presence of the HC-Pro transgene (HC-Pro) or a transgene that produces double-stranded ntRAV RNA (dsRAV) and thereby induces silencing of the ntRAV gene. In an otherwise WT background, GUS silencing in line 6b5 begins between 14 and 24 days after germination as indicated by the reduced level of GUS mRNA and the simultaneous appearance of the GUS siRNAs, which are diagnostic of RNA silencing. HC-Pro blocks the onset of silencing and prevents siRNA accumulation. In contrast, the presence of the dsRAV transgene accelerates GUS silencing as indicated by the reduced levels of GUS mRNA even at 7 days after germination and the appearance of GUS siRNAs by 14 days after germination.

FIG. 3 shows the effect of reducing ntRAV expression on sense transgene silencing of the reporter gene GUS in tobacco transgenic line 6b5. Histochemical staining to localize GUS expression in plants at 24 days after germination is shown in the upper part of the figure. Shown at the far left is a leaf from the 6b5 transgenic plant that also expresses HC-Pro, a viral suppressor of RNA silencing (HC-Pro X 6b5). This leaf is dark colored throughout because silencing of the GUS gene is blocked. The second leaf from the left shows a leaf from a 6b5 transgenic plant that also overexpresses the ntRAV gene and is also suppressed for RNA silencing (ntRAV X 6b5). The third leaf from the left is from the 6b5 line in an otherwise wildtype background (WT X 6b5). This leaf shows the initiation of GUS silencing in the veins of the leaf: thus, the veins of the plants are not dark colored in some places due to lack of GUS activity. The last leaf on the right is from the 6b5 line that also carries a transgene that expresses double-stranded (ds) RNA for the endogenous ntRAV gene (dsRAV X 6b5). This leaf shows more extensive silencing of the GUS transgene as indicated by more extensive loss of color in the veins.

Molecular data from the same plants is shown in the lower part of the figure. The level of GUS mRNA and GUS siRNAs is shown in the sense-transgene silenced 6b5 transgenic line at 7, 14 or 24 days post-germination in an otherwise wildtype background (wt) or in the presence of the HC-Pro transgene (HC-Pro) or a transgene that produces double-stranded ntRAV RNA (dsRAV) and thereby induces silencing of the ntRAV gene. In an otherwise WT background, GUS silencing in line 6b5 begins between 14 and 24 days after germination as indicated by the reduced level of GUS mRNA and the simultaneous appearance of the GUS siRNAs, which are diagnostic of RNA silencing. HC-Pro blocks the onset of silencing and prevents siRNA accumulation. In contrast, the presence of the dsRAV transgene accelerates GUS silencing as indicated by the reduced levels of GUS mRNA even at 7 days after germination and the appearance of GUS siRNAs by 14 days after germination.

Figure 4:
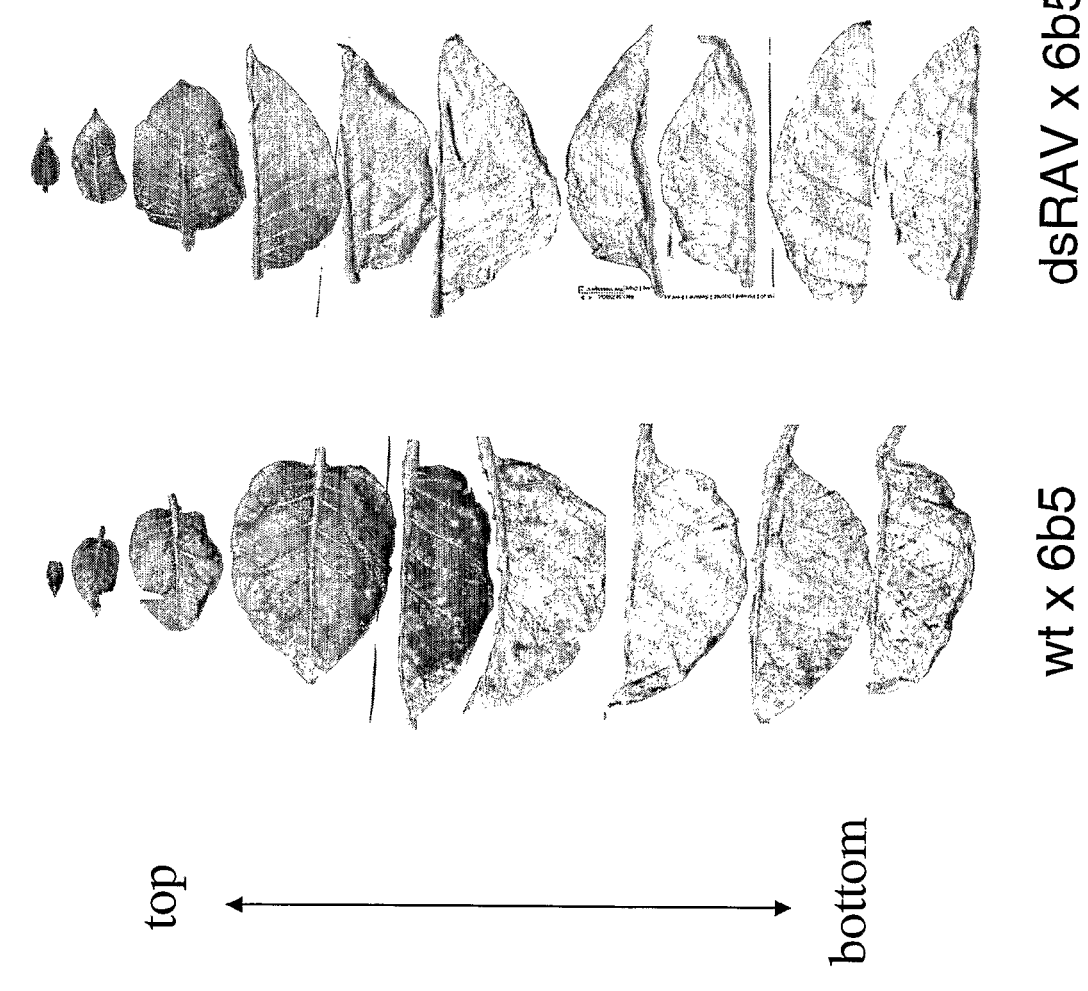
FIG. 4 illustrates the effectiveness of RNA silencing in tobacco plants, and contrasts silencing in a wild type 6b5 cross (wt x 6b5) with silencing in a knockdown ntRAV plant (dsRAV x 6b5), showing that silencing proceeds from the bottom to the top of the plant, and is visually more advanced in the knockdown ntRAV plant than in the wild type plant.

An illustration of the effectiveness of RNA silencing in tobacco plants is shown in FIG. 4, where silencing in a wild type 6b5 cross (wt x 6b5) is contrasted with silencing in a knockdown ntRAV plant (dsRAV x 6b5), and it can be seen that silencing proceeds from the bottom to the top of the plant, and is visually more advanced in the knockdown ntRAV plant than in the wild type plant.

Example 4

This example illustrates the effect on sense transgene silencing of a knockout of the RAV-2 gene in *Arabidopsis thaliana*.

FIG. 9 (left-most box) shows histochemical staining of an *Arabidopsis* seedling of a transgenic line called L1. The L1 line is an example of a sense transgene silenced line which is silenced for the GUS gene. At this early stage of development, the silencing has just begun and the younger leaves of the seedling are expressing slightly less GUS and are therefore are a lighter blue color. In contrast, an L1 seedling which is mutant for the RAV-2 (At1g68840) gene due to a T-DNA insertion within that gene shows a much more advanced silencing at the same developmental stage (FIG. 9, right-most box). Thus, a knock-out of the *Arabidopsis thaliana* RAV-2 gene enhances sense transgene silencing.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense. In addition, it should be understood that aspects of the various embodiments may be interchanged both in whole or in part.

---

What is claimed is:

1. A chimeric gene comprising the nucleotide sequence of SEQ ID NO: 1 operably linked to suitable regulatory sequences, the regulatory sequences comprising a transcription initiation region that is heterologous to SEQ ID NO: 1.

2. A recombinant vector for transformation of plant cells, the vector comprising the chimeric gene of claim 1.

3. A plant cell comprising the chimeric gene of claim 1.

4. A plant seed comprising the plant cell of claim 3.

* * * * *